United States Patent [19]

Selva et al.

[11] Patent Number: 5,139,778
[45] Date of Patent: Aug. 18, 1992

[54] ANTIBIOTIC GE 2270 FACTORS $A_1$, $A_2$, $A_3$ AND H

[75] Inventors: Enrico Selva, Gropello Cairoli; Paolo Tavecchia, Rho, both of Italy

[73] Assignee: Gruppo Lepetit SpA, Milan, Italy

[21] Appl. No.: 547,647

[22] Filed: Jul. 2, 1990

[30] Foreign Application Priority Data

Jul. 4, 1989 [EP] European Pat. Off. ........ 89112171.7

[51] Int. Cl.$^5$ ............................................. A61K 35/70
[52] U.S. Cl. .................................... 424/117; 424/115; 424/123; 424/124
[58] Field of Search ................ 424/117, 115, 123, 124

[56] References Cited

U.S. PATENT DOCUMENTS

| | | | |
|---|---|---|---|
| 4,594,187 | 6/1986 | Strazzolini et al. | 536/332 |
| 4,607,012 | 8/1986 | Selva et al. | 424/115 |
| 4,692,333 | 9/1987 | Pirali et al. | 424/122 |

Primary Examiner—Jerome D. Goldberg
Attorney, Agent, or Firm—J. Michael Dixon

[57] ABSTRACT

The present invention is directed to new antibiotic substances denominated antibiotic GE 2270 factors $A_1$, $A_2$, $A_3$ and H, the additional salts thereof, the pharmaceutical compositions thereof and their use as medicaments, particularly in the treatment of infectious diseases involving microorganisms susceptible to them.

11 Claims, 13 Drawing Sheets

FIG. 10 ANTIBIOTIC GE 2270 FACTOR A₃

ANTIBIOTIC GE 2270 FACTOR H

ANTIBIOTIC GE 2270 FACTORS $A_1$, $A_2$, $A_3$ AND H

The present invention is directed to new antibiotic substances denominated antibiotic GE 2270 factors $A_1$, $A_2$, $A_3$ and H, the addition salts thereof, the pharmaceutical compositions thereof and their use as medicaments, particularly in the treatment of infectious diseases involving microorganisms susceptible to them.

The compounds of the invention are also active as growth promotant agents in animals, such as poultry, swine, ruminants, etc.

Another object of this invention is a process for preparing antibiotic GE 2270 factors $A_1$, $A_2$, $A_3$ or H by selective transformation of antibiotic GE 2270 factor A. This substance is, in turn, prepared by culturing a sample of Planobispora rosea ATCC 53773 or a producing variant or mutant thereof and isolating the desired antibiotic substance from the mycelium and/or the fermentation broth. Planobispora rosea ATCC 53773 was isolated from a soil sample and deposited on Jun. 14, 1988 with the American Type Culture Collection (ATCC), 12301 Parklawn Drive, Rockville, Md. 20852 Maryland, U.S.A., under the provisions of the Budapest Treaty.

The strain has been accorded accession number ATCC 53773.

Antibiotic GE 2270 factor A and Planobispora rosea ATCC 53773 are described in European Patent application Publication No. 359062.

In view of the similarities between the antimicrobial activity of antibiotic GE 2270 factor $A_1$, $A_2$, $A_3$ and H and the corresponding pharmaceutically acceptable salts, when available, in the present application when dealing with the biological properties of antibiotic GE 2270 factors $A_1$, $A_2$, $A_3$ or H, also the corresponding salts are included and vice versa, when dealing with the biological properties of a pharmaceutically acceptable addition salt of antibiotic GE 2270 factor $A_1$, $A_2$, $A_3$ or H, also the corresponding "non-addition salt" form is encompassed.

In particular, antibiotic GE 2270 factor $A_3$ can form base addition salts according to the usual procedures.

Representative examples of these bases are: alkali metal of alkaline-earth metal hydroxides such as sodium, potassium, calcium, magnesium, and barium hydroxide; ammonia and aliphatic, alicyclic or aromatic organic amines such as methylamine, dimethylamine, trimethylamine, and picoline. Also the salts with basic aminoacids or derivatives thereof such as arginine, lysine or ornithine are encompassed by the present definition of base addition salts.

The transformation of the "non-salt" compounds of the invention into the corresponding addition salts, and the reverse, i.e. the transformation of an addition salt of a compound of the invention into the non-salt form, are within the ordinary technical skill and are encompassed by the present invention.

A base addition salt of antibiotic GE 2270 factor $A_3$ can be prepared for instance by dissolving or suspending the non-salt form in an aqueous solvent and adding a slight molar excess of the selected base. The resulting solution or suspension is then lyophilized to recover the desired salt.

In case the final salt is unsoluble in a solvent where the non-salt form is soluble, it is recovered by filtration from the organic solution of the non-salt form after addition of the stoichiometric amount of a slight molar excess of the selected base.

The non-salt form can be prepared from a corresponding base salt dissolved in an aqueous solvent which is then neutralized to free the non-salt form.

When following the neutralization the elimination of the excess of acid or base is necessary, a common desalting procedure may be employed.

For example, column chromatography on silanized silica gel, non-functionalized polystyrene, acrylic and controlled pore polydextrane resins (such as Sephadex ® LH 20) or activated carbon may be conveniently used. After eluting the undesired salts with an aqueous solution, the desired product is eluted by means of a linear gradient or a step gradient of a mixture of water and a polar or a polar organic solvent, such as acetonitrile/water from 50:50 to about 100% acetonitrile.

The compounds of the invention are prepared from antibiotic GE 2270 factor A under selective chemical transformation conditions.

More particularly, antibiotic GE 2270 factors $A_1$, $A_2$ and $A_3$ are prepared by antibiotic GE 2270 factor A under selective hydrolysis conditions, while by selective cleavage under reducing conditions antibiotic GE 2270 factor H is obtained from antibiotic GE 2270 factor A.

Generally, the above mentioned hydrolytic conditions involve the use of mixtures of buffered or unbuffered aqueous acid media and polar organic solvents. The reaction temperature varies depending on such factors as the strength and the concentration of the acid employed, and is generally comprised between $-10°$ C. and $90°$ C. Also the reaction time varies considerably depending on the other parameters such as temperature and acid strength and concentration; generally it may vary from a few minutes to several hours.

In general, when milder hydrolysis conditions are employed, e.g. shorter time and lower temperature or lower acid strength or concentration, antibiotic GE 2270 factor $A_1$ is normally obtained, while under stronger conditions antibiotic GE 2270 factor $A_2$ is obtained. To obtain antibiotic GE 2270 factor $A_3$ under acid hydrolytic conditions still more drastic conditions are necessary.

However, since the reaction course can be monitored according to the usual procedures, e.g. TLC or HPLC, by following the disappearance of the starting material and/or appearance of the final products, the skilled technician is capable of deciding when the reaction can be considered as complete and the recovery procedure may be started.

Examples of buffered or unbuffered aqueous acidic media are aqueous solutions or suspensions of mineral or organic acids such as hydrogen halides, e.g. hydrogen chloride, bromide or iodide; phosphoric acids; sulfuric acid: $(C_1-C_6)$ aliphatic, halogenated$(C_2-C_5)$aliphatic or arylic acids; $(C_2-C_6)$ alkylsulfonic or arylsulfonic acids; cationic exchange resins in the acid form, and the products of partial salification of polyprotonic acids, i.e., salts having acidic reaction in water, e.g. an alkali-metal hydrogen phosphate or dihydrogen phosphate, alkali metal hydrogen sulfate and the like. Examples of alkali-metals are sodium and potassium.

Representative examples Of the $(C_1-C_6)$ aliphatic acids mentioned above are formic acid, acetic acid, propionic acid, butyric acid, isobutyric acid, valeric acid, isovaleric acid, trimethylacetic acid, and the like.

Representative examples of the halogenated ($C_2-C_5$) aliphatic acids mentioned above are mono- or polychloro, bromo or iodo aliphatic acids such as fluoroacetic acid, chloroacetic acid, difluoroacetic acid, dichloroacetic acid, trifluoroacetic acid, trichloroacetic acid, pentafluoropropionic acid, 2,2,3,4,4,4-hexafluorobutyric acid, heptafluorobutyric acid, and the like.

Representative examples of arylic acids are benzoic acid and mono- or poly- substituted benzoic acids such as chlorobenzoic acid, methylbenzoic acid, phthalic acid, terphthalic acid, benzylacetic acid and the like.

Representative examples of the sulfonic acids mentioned above are: methanesulfonic acid, trifluoromethanesulfonic acid, p-toluenesulfonic acid, cyclohexanesulfonic acid, camphorsulfonic acid, alpha- and beta-naphthalenesulfonic acid.

The "cationic exchange resins" mentioned above are commonly known and commercially available resins such as sulfonated styrenic and styrene-divinyl benzenic resins in the acid form.

Suitable organic solvents as mentioned above are such that:
a) they may at least partially solubilize the starting materials;
b) the products, once obtained, either separate or may be separated according to usual techniques, and
c) in any case, they do not unfavorably interfere with the reaction course.

Examples of said organic polar solvents are cyclic oxygen containing aliphatic solvents such as dioxane (i.e. diethylenedioxide), tetrahydrofuran and the like; lower alkanols; phenyl substituted lower alkanols; lower alkyl carboxamides; lower alkyl sulfoxamides; lower alkyl phosphoramides; lower alkyl sulfoxides and lower alkyl sulfones, and the like, and mixtures thereof. The term "lower alkyl" as used above, represents preferably alkyl groups of 1 to 6 carbon atoms. Examples of lower alkanols are $C_1-C_6$ alkanols such as methanol, ethanol, propanol, 1-methylethanol, butanol and 2-methylpropanol.

Examples of phenyl substituted lower alkanols are the following: benzyl alcohol, m-chlorobenzyl alcohol, o-fluorobenzyl alcohol, m-fluorobenzyl alcohol, p-fluorobenzyl alcohol, m-methylbenzyl alcohol, m-methoxybenzyl alcohol, o-ethoxybenzyl alcohol, m-butoxybenzyl alcohol, p-tert.butoxybenzyl alcohol, p-tert.butylbenzyl alcohol, phenethyl alcohol, o-chlorophenethyl alcohol, m-chlorophenetyl alcohol, o-methoxyphenethyl alcohol, m-methoxyphenethyl alcohol, o-propylphenethyl alcohol, o-ethoxyphenethyl alcohol, p-fluorophenethyl alcohol, p-bromophenethyl alcohol, o-propoxyphenethyl alcohol, o-butoxyphenethyl alcohol, 1-(p-isopropylphenyl)ethanol, 3-phenyl-1-propanol, 2-phenyl-1-propanol, 4-phenyl-1-butanol and 3-phenyl-1-butanol.

Examples of lower alkyl carboxamides are dimethylformamide, diethylformamide and the like. A preferred lower alkyl sulfoxide is dimethyl sulfoxide, a preferred lower alkyl sulfone is dimethylsulfone and a preferred lower alkyl phosphoramide is hexamethyl phosphoramide.

A preferred embodiment of the invention is represented by a process for preparing antibiotic GE 2270 factor A: which comprises contacting antibiotic GE 2270 factor A with a buffered or unbuffered acid medium in the presence of a polar organic solvent at a temperature between $-10°$ C. and $50°$ C., and preferably between $4°$ C. and $25°$ C. The reaction time, which varies considerably depending on the other specific reaction parameters, is, in this case, generally between 5 min and 16 h.

Another preferred embodiment of the invention is represented by a process for preparing antibiotic GE 2270 factor $A_2$ which comprises contacting antibiotic GE 2270 factor A or factor $A_1$ with a buffered or unbuffered acid medium in the presence of a polar organic solvent at a temperature between $40°$ C. and $90°$ C., and preferably between $50°$ C. and $70°$ C. The reaction time, which varies considerably depending on the other specific reaction parameters, is, in this case, generally between 12 h and 24 h.

In the case of the conversion of factor $A_1$ into factor $A_2$ under the above conditions, it appears that ammonia is lost by the molecule of the starting material.

A further preferred embodiment of the invention is represented by a process for preparing antibiotic GE 2270 factor $A_3$ which comprises contacting antibiotic GE 2270 factor A with a buffered or unbuffered acid medium in the presence of a polar organic solvent at a temperature between $40°$ C. and $90°$ C., and preferably between $65°$ C. and $80°$ C. The reaction time, which varies considerably depending on the other specific reaction parameters, is, in this case, generally between 8 h and 48 h.

In this case however, the conversion yields are generally low (5-15% molar yield) even by using strong reaction conditions.

A preferred method for preparing antibiotic 2270 factor $A_3$ with acceptable yields and purity is represented by the treatment of antibiotic GE 2270 factor $A_2$ under basic hydrolytic conditions in the presence of polar organic solvents. Examples of polar organic solvents are as reported above, while the basic conditions can be imparted by any aqueous basic solution or suspension.

Examples of base that can conveniently be employed are inorganic or organic bases such as alkali-metal or earth-metal hydroxides; salts having basic reaction in water such as alkali-metal carbonates or bicarbonates; ammonia and aliphatic or aromatic amines such as alkyl amines (e.g. dimethylamine, diethylamine, triethy)amine, trimethylamine) and picolines. Examples of alkali-earth metals are calcium and magnesium.

The following specific reaction conditions are given simply to further illustrate the process of the invention.

In the following tables:

"R.T." means "room temperature" i.e. approximately $15°$ C.$-25°$ C.

"EtOH" means "ethanol"

"TFA" means "trifluoroacetic acid"

"AcOH" means "acetic acid"

"Dowex" 50W$\times$2 (H+) is a cation exchange resin in the acid form

"TEA" means "triethylamine".

Specifically preferred reaction conditions for the preparation of antibiotic GE 2270 factor $A_1$ from factor A are the following:

| Temperature °C. | Time | Acid medium | Polar solvent |
|---|---|---|---|
| R.T. | 5 min | 0.2M HCl | EtOH/$H_2O$ 9/1 |
| R.T. | 15 min | TFA/dioxane/$H_2O$ 1/4/5 | |
| R.T. | 15 min | 0.5N $H_2SO_4$ | Dioxane/$H_2O$/ 1/1 |

-continued

| Temperature °C. | Time | Acid medium | Polar solvent |
|---|---|---|---|
| R.T. | 15 min | 0.25M H$_3$PO$_4$ | Dioxane/H$_2$O/ 1/1 |
| 50 | overnight | 0.5M NH$_4$Cl | Dioxane/H$_2$O/ 1/1 |

Specifically preferred reaction conditions for the preparation of antibiotic GE 2270 factor A$_2$ from factor A or A$_1$ or a mixture thereof are the following:

| Temperature °C. | Time | Acid medium | Polar solvent |
|---|---|---|---|
| 60° C. | 24 h | AcOH/EtOH (95%) | |
| 80° C. | overnight | AcOH/H$_2$O. 1/1 | |
| 50° C. | overnight | TFA/dioxane/H2O, 1/4/5 | |
| 50° C. | overnight | 0.25M H$_3$PO$_4$ | Dioxane/H$_2$O/ 1/1 |
| 50° C. | overnight | 0.5M NH$_4$Cl | Dioxane/H$_2$O/ 1/1 |
| 50° C. | overnight | Dowex 50Wx2 (H$^+$) | Dioxane/H$_2$O/ 1/1 |
| 50° C. | overnight | p.toluene-sulfonic acid | Dioxane/H$_2$O/ 1/1 |

Specifically preferred reaction conditions for the preparation of antibiotic GE 2270 factor A$_3$ from factor A$_2$ are the following:

| Temperature °C. | Time | Acid medium | Polar solvent |
|---|---|---|---|
| R.T. | 15 min | NaOH | Dioxane/H$_2$O 1/1 |
| R.T. | 1 h | 0.5M Na$_2$CO$_3$ | Dioxane/H$_2$O 1/1 |
| R.T. | overnight | 0.5M NaHCO$_3$ | Dioxane/H$_2$O 1/1 |
| R.T. | overnight | 0.5M TEA | Dioxane/H$_2$O 1/1 |
| 80° C. | 1 h | 0.5M NaHCO$_3$ | Dioxane/H$_2$O 1/1 |
| 80° C. | 1 h | 0.5M TEA | Dioxane/H$_2$O 1/1 |

Specifically preferred reaction conditions for the preparation of antibiotic GE 2270 factor A$_3$ from factor A are the following:

| Temperature °C. | Time | Acid medium | Polar solvent |
|---|---|---|---|
| 50° C. | overnight | TFA/H$_2$O/dioxane 1/4/5 | |
| 70° C. | overnight | Dowex 50Wx2 (H$^+$) | Dioxane/H$_2$O/ 1/1 |
| 70° C. | overnight | 0.5N H$_2$SO$_4$ | Dioxane/H$_2$O/ 1/1 |

Antibiotic GE 2270 factor H is prepared by antibiotic GE 2270 factor A by controlled cleavage under reducing conditions.

Preferred reducing conditions are given by alkali metal borohydrides, such as sodium or potassium borohydride, in a compatible polar organic solvent, such as one of those indicated above. A preferred solvent is aqueous tetrahydrofuran and a preferred borohydride is sodium borohydride.

The compounds of the invention are recovered at the end of the preparation process according to known per se techniques which includes extraction with solvents, precipitation by means of precipitating agents, by changing the pH, and/or by concentration, and chromatographic techniques such as partition chromatography, reverse-phase partition chromatography, ion-exchange, molecular exclusion chromatography, preparative HPLC and the like.

Physico-chemical characteristics of antibiotic GE 2270 factor A$_1$

A) ultraviolet absorption spectrum which is shown in FIG. 1 of the accompanying drawings, and exhibits the following absorption maxima:

| | Lambda max (nm) |
|---|---|
| 0.1M HCl | about 240 (shoulder) 310 |
| 0.1M KOH | about 245 (shoulder) 311 |
| Phosphate buffer pH 7.4 | about 245 (shoulder) 310 |
| Methanol | about 215 (shoulder) about 240 (shoulder) 309 |

B) infrared absorption spectrum in nujol mull which is shown in FIG. 2 of the accompanying drawings and exhibits the following absorption maxima (cm$^{-1}$): 3700–3000; 3000–2800 (nujol); 1650; 1535; 1505; 1460 (nujol); 1375 (nujol); 1310; 1240; 1190; 1165; 1130–1000; 980; 930; 840; 805; 750; 720 (nujol); 700;

C) $^1$H-NMR spectrum which is shown in FIG. 3 and exhibits the following groups of signals at 500 MHz recorded in DMSO-D$_6$ (hexadeuterodimethylsulfoxide) using TMS as the internal standard (0.00 ppm); the multiplicity for each signal is also reported below (s=singlet; d=doublet; m=multiplet; dd=doublet of doublets; br s=broad singlet):

0.84, d, 0.87, d; 1.35, m; 1.91, m; 2.08, m; 2.16, m; 2.46, d; 2.58, s; 2.70, dd; 3.38, s; 3.76, m; 3.84, m; 4.26, dd; 4.33, m; 4.89, m; 4.97, s; 5.00, dd; 5.20, dd; 5.22, dd; 5.28 (2 protons), m; 6.01, d; 7.07, s; 7.2, s; 7.34, s; 7.22–7.38 (6 protons), m; 8.29, s; 8.39, d; 8.44, m; 8.45, d; 8.54, s; 8.60, s; 8.66, d; 9.69, d; 8.99, d.

D) retention-time (R$_t$) of 13.4 min when analyzed by reverse phase HPLC under the following conditions:
column: Ultrasphere ODS (reverse phase silanized silica gel; 5 micrometer) Altex (Beckman) 4.6 mm (i.d.)×250 mm
pre-column: Brownlee Labs RP 18 (octadecylsilane silica gel; 5 micrometer)
eluent A: acetonitrile:18mM NaH$_2$PO$_4$, 70:30 (v/v), adjusted to pH 7.0
eluent B: acetonitrile:18mM NaH$_2$PO$_4$ 10:90 (v/v), adjusted to pH 7.0
elution mode: linear gradient of eluent A in eluent B from 45% to 70% in 20 min
flow rate: 1.8 ml/min
U.V. detector: 254 nm
internal standard: Chloramphenicol (R$_t$=3.6 min)

E) elemental analysis, after the sample has been previously dried at about 140° C. under inert atmosphere, which indicated the following composition: carbon, hydrogen, nitrogen, sulfur.

F) FAB-MS analysis showing the low mass isotope of the protonated molecular ion at m/z 1308 mass units; all the other peaks above 800 m/z mass units in the spectrum, not counting isotope peaks, were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode.

Physico-chemical characteristics of antibiotic GE 2270 factor $A_2$

A) ultraviolet absorption spectrum, which is shown in FIG. 4 of the accompanying drawings, and exhibits the following absorption maxima:

|  | Lambda max (nm) |
|---|---|
| 0.1M HCl | about 245 (shoulder) |
|  | 309 |
| 0.1M KOH | about 245 (shoulder) |
|  | 309 |
| Phosphate buffer pH 7.4 | about 245 (shoulder) |
|  | 309 |
| Methanol | about 215 (shoulder) |
|  | about 242 (shoulder) |
|  | 306 |

B) infrared absorption spectrum in nujol mull which is shown in FIG. 5 of the accompanying drawings and exhibits the following absorption maxima (cm$^{-1}$): 3700–3000; 3000–2800 (nujol); 1725; 1655; 1590–1480; 1460 (nujol); 1410; 1375 (nujol); 1335; 1305; 1265–1130; 1090; 1050; 1015; 980; 945; 930; 840; 805; 745; 720 (nujol); 700;

C) $^1$H-NMR spectrum which is shown in FIG. 6 and exhibits the following groups of signals at 500 MHz recorded in DMSO-D$_6$ hexadeuterodimethylsulfoxide) using TMS as the internal standard (0.00 ppm); the multiplicity for each signal is reported between parenthesis (s=singlet; d=doublet; m=multiplet; dd=doublet of doublets; br s=broad singlet):

0.83, d; 0.86, d; 1.30, m; 1.82, m;; 1.90, m; 2.17, m; 2.46, d; 2.57, s; 2.70, dd; 3.37, s; 3.40, m; 3.48, m; 3.77, dd: 4.24, m; 4.28, dd; 4.52, d; 4.53, br s; 4.67, d; 4.96, s; 4.98, dd; 5.19, m; 5.21, m; 5.28, m; 6.01, d; 7.34, s; 7.22–7.35, m; 8.26, d; 8.28, s; 8.42, d; 8.45, s; 8.59, s; 8.67 (2 protons), d; 8.73, s; 9.00, d;

D) retention-time (Rr) of 17.0 min when analyzed by reverse phase HPLC under the following conditions:
column: Ultrasphere ODS (reverse phase silanized silica gel; 5 micrometer) Altex (Beckman) 4.6 mm (i.d.)×250 mm
pre-column: Brownlee Labs RP 18 (octadecylsilane silica gel; 5 micrometer)
eluent A: acetonitrile:18mM NaH$_2$PO$_4$, 70:30 (v/v), adjusted to pH 7.0
eluent B: acetonitrile:18mM NaH$_2$PO$_4$ 10:90 (v/v), adjusted to pH 7.0
elution mode: linear gradient of eluent A in eluent B from 45% to 70% in 20 min
flow rate: 1.8 ml/min
U.V. detector: 254 nm
internal standard: Chloramphenicol ($R_t$=3.6 min)

E) elemental analysis, after the sample has been previously dried at about 140° C. under inert atmosphere, which indicated the following composition: carbon, hydrogen, nitrogen, sulfur.

F) FAB-MS analysis showing the low mass isotope of the protonated molecular ion at m/z 1291 mass units; all the other peaks above 800 M/Z mass units in the spectrum, not counting isotope peaks, were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode.

Physico-chemical characteristics of antibiotic GE 2270 factor $A_3$

A) ultraviolet absorption spectrum which is shown in FIG. 7 of the accompanying drawings, and exhibits the following absorption maxima:

|  | Lambda max (nm) |
|---|---|
| 0.1M KOH | 240 (shoulder) |
|  | 309 |
|  | 330 (shoulder) |
| Phosphate buffer pH 7.4 | 240 (shoulder) |
|  | 309 |
|  | 330 shoulder |
| Methanol | 240 (shoulder) |
|  | 309 |
|  | 340 (shoulder) |

B) infrared absorption spectrum in nujol mull which is shown in FIG. 8 of the accompanying drawings and exhibits the following absorption maxima (cm$^{-1}$): 3700–3140; 3110; 3020–2750 (nujol); 1720; 1655; 1590–1520; 1500; 1460 (nujol); 1375 (nujol) 1270–1200; 1130–1030; 1020; 980; 930; 840; 805; 750; 720 (nujol); 700;

C) $^1$H-NMR spectrum which is shown in FIG. 9 and exhibits the following groups of signals (in ppm) at 500 MHz recorded in DMSO-D$_6$ hexadeuterodimethylsulfoxide) using TMS as the internal standard (0.00 ppm); the number of protons and multiplicity for each signal is also reported below (s=singlet; d=doublet; m=multiplet; dd=doublet of doublets; br s=broad singlet):

9.02,1H (d); 8.71,1H (d); 8.70,1H (d); 8.65,1H (s); 8.57,1H (s); 8.46,1H (m); 8.38,1H (d); 8.28,1H (d); 8.25,1H (s); 7.38,1H (m); 7.37,1H (s); 7.36–7.20,5H (m); 6.05,1H (br s); 5.31,1H (m); 5.27,1H (dd); 5.20,1H (dd); 5.03,1H (d); 4.99,2H (s); 4.32,1H (dd); 3.82,1H (dd); 3.38,3H (s); 2.74,1H (dd); 2.60,3H (s); 2.49,3H (d); 2.17,1H (m); 1.35,1H (m); 0.88,3H (d); 0.84,3H (d);

D) retention-time ($R_t$) of 7.1 min when analyzed by reverse phase HPLC under the following conditions:
column: Ultrasphere ODS (reverse phase silanized silica gel; 5 micrometer) Altex (Beckman) 4.6 mm (i.d.)×250 mm
pre-column: Brownlee Labs RP 18 (octadecylsilane silica gel; 5 micrometer)
eluent A: acetonitrile:18mM NaH$_2$PO$_4$, 70:30 (v/v), adjusted t pH 7.0
eluent B: acetonitrile:18mM NaH$_2$PO$_4$ 10:90 (v/v), adjusted to pH 7.0
elution mode: linear gradient of eluent A in eluent B from 45% to 70% in 20 min
flow rate: 1.8 ml/min
U.V. detector: 254 nm
internal standard: Chloramphenicol ($R_t$=3.6 min)

E) elemental analysis, after the sample has been previously dried at about 140° C. under inert atmosphere, which indicated the following composition: carbon 51.27%, hydrogen 4.02%, nitrogen 14.94%, sulfur.

F) FAB-MS analysis showing the low mass isotope of the protonated molecular ion at m/z 1125 mass units; all the other peaks above 800 m/z mass units in the spectrum, not counting isotope peaks, were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode.

G) $^{13}$C-NMR spectrum which is reported in FIG. 10 of the accompanying drawings exhibiting the following groups of signals (ppm) at 125 MHz in DMSO-d$_6$ TMS as the internal reference (0.00 ppm), 171.2; 169.9; 169.6; 168.5; 167.8; 165.7; 164.8; 162.2; 161.4; 161.3; 160.5; 160.4; 153.5; 150.4; 150.1; 149.5; 149.1; 147.0; 143.8; 142.1; 141.8; 141.4; 141.0; 139.6; 131.8; 128.0 (2 carbons); 127.7; 127.6; 126.9; 126.8 (2 carbons); 123.1; 118.7; 116.4; 73.9; 67.4; 58.7; 58.3; 55.5; 48.2; 41.2; 37.7; 34.1; 25.9; 18.5; 18.0; 12.0;

H) a specific optical rotation $[\alpha]^{20}{}_D$ of +182.5 in CHCl$_3$ +10% CH$_3$OH.

Physico-chemical characteristics of antibiotic GE 2270 factor H

A) ultraviolet absorption spectrum, which is shown in FIG. 11 of the accompanying drawings, and exhibits the following absorption maxima:

| | Lambda max (nm) |
|---|---|
| 0.1M HCL | 248 |
| | 303 |
| 0.1M KOH | about 245 (shoulder) |
| | 310 |
| Phosphate buffer pH 7.4 | about 240 (shoulder) |
| | 312 |
| Methanol | about 215 (shoulder) |
| | about 240 (shoulder) |
| | 309 |

B) infrared absorption spectrum in nujol mull which is shown in FIG. 12 of the accompanying drawings and exhibits the following absorption maxima (cm$^{-1}$):

3700-3000; 3000-2800 (nujol); 1655; 1590 1480; 1460 (nujol) 1375 (nujol); 1310; 1220; 1190; 1130-1000; 980; 930; 840; 820-680; 720 (nujol); 640;

C) $^1$H-NMR spectrum which is shown in FIG. 13 and exhibits the following groups of signals (ppm) at 500 MHz recorded in DMSO-D$_6$ (hexadeuterodimethylsulfoxide) using TMS as the internal standard (0.00 ppm); the multiplicity for each signal is also reported below (s=singlet; d=doublet; m=multiplet; dd=doublet of doublets; br s=broad singlet): 0.83, d; 0.87 d; 1.30, m; 2.16, m; 2.46, d; 2.58, s; 2.70, dd; 3.38, s; 3.52, m; 3.61, m; 3.77, dd; 4.25, m; 4.30, m; 4.35, m; 4.47, m; 4.88, m; 4.97, s; 4.99, dd; 5.20, m; 5.23, m; 5.28, m; 6.02, d; 7.36, s; 7.22-7.40, m; 8.26, d; 8.28, s; 8.42, d; 8.43, m; 8.47, s; 8.60, s; 8.67, d; 9.02, d;

D) retention-time (Rr) of 18.0 min when analyzed by reverse phase HPLC under the following conditions:
column: Ultrasphere ODS (reverse phase silanized silica gel; 5 micrometer) Altex (Beckman) 4.6 mm (i.d.)×250 mm
pre-column: Brownlee Labs RP 18 (octadecylsilane silica gel; 5 micrometer)
eluent A: acetonitrile:18mM NaH$_2$PO$_4$, 70:30 (v/v), adjusted to pH 7.0
eluent B: acetonitrile:18mM NaH$_2$PO$_4$ 10:90 (v/v), adjusted to pH 7.0
elution mode: linear gradient of eluent A in eluent B from 45% to 70% in 20 min
flow rate: 1.8 ml/min
U.V. detector: 254 nm
internal standard: Chloramphenicol (R$_t$=3.6 min)

E) elemental analysis, after the sample has been previously dried at about 140° C. under inert atmosphere, which indicated the following composition: carbon, hydrogen, nitrogen, sulfur.

F) FAB-MS analysis showing the low mass isotope of the protonated molecular ion at m/z 1180 mass units; all the other peaks above 800 m/z mass units (not counting isotope peaks) in the spectrum were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode.

The antimicrobial activity of the compounds of the invention can be demonstrated by a series of standard tests in vitro.

MIC for *Clostridium difficile, Propionibacterium acnes,* and *Bacteroides fragilis* are determined by agar dilution (inocula 10$^4$/10$^5$ CFU/spot). MIC for other organisms are determined by microbroth dilution (inocula 10$^4$ to 10$^5$ CFU/ml). Incubation times are 18-24 h, except for *Neisseria gonorrhoeae, Branhamella catarrhalis, Haemophilus influenzae. C. difficile, P. acnes, B. fragilis* (48h). All organisms are incubated at 37° C. *N. gonorrhoeae* and *H. influenzae* are incubated in a 5% CO$_2$ atmosphere, anaerobes in an anaerobic gas mixture. Media used are: Iso-Sensitest broth (Oxoid) (*Staphylococcic, Streptococcus faecalis, Escherichia coli, Pseudomonas aeruginosa. Proteus vulgaris, Klebsiella pneumoniae*); Todd-Hewitt broth (Difco) (other streptococci); Mueller Hinton broth (BBL) (*Branhamella catarrhalis*); GC base broth (Difco) +1% IsoVitalex (BBL) (*N. gonorrhoeae*); brain heart infusion broth (Difco) +1% Supplement C (Difco) (*H. influenzae*); AC medium (Difco) (*C. perfringens*); Wilkins-Chalgren agar (Difco) (other anaerobes) (T.D. Wilkins and S. Chalgren, Antimicrob. Ag. Chemother. 10, 926, 1976). *Chlamydia trachomatis* was cultivated in microtiter plates on cycloheximide treated McCoy cell monolayers, in Eagle's MEM medium (Gibco) with 10% fetal calf serum, in a 5% CO$_2$ atmosphere. Inocula were prepared so as to give 30-60 inclusions per 300×microscope field. After 48 h, chlamydial inclusions were stained with fluorescein-labeled monoclonal antibody to the major outer membrane protein (Syva) and counted by fluorescence microscopy. The MIC was taken as the concentration at which inclusions were no longer seen and cellular morphology was normal.

The minimal inhibitory concentrations (MIC, microgram/ml) for some microorganisms are reported below in Table I.

TABLE I

| Strain | M.I.C. (microgram/ml) Antibiotic GE 2270 factor A$_1$ |
|---|---|
| *Staph. aureus* Tour L165 | 0.06 |
| *Staph. aureus* Tour L165 + 30% bovine serum | 0.5 |
| *Staph. epidermidis* L147 ATCC 12228 | 0.06 |
| *Staph. haemolyticus* L602 clin. isolate | ≦0.13 |
| *Strep. pyogenes* C203 | >128 |
| *Strep. pneumoniae* UC41 | >128 |
| *Strep. faecalis* ATCC 7080 | 0.06 |
| *Strep. mitis* L796 | 16 |
| *Clostridium perfringens* ISS 30543 | 0.06 |
| *Propionibacterium acnes* ATCC 6919 | 0.03 |
| *Bacteroides fragilis* ATCC 23745 | >128 |
| *Neisseria gonorrhoeae* ISM68/126 | >128 |
| *Ureaplasma urealyticum* L 1479 | >128 |
| *Escherichia coli* SKF 12140 | >128 |
| *Pseudomonas aeruginosa* ATCC 10145 | >128 |
| *Proteus vulgaris* ATCC 881 | >128 |

TABLE I-continued

| Strain | |
|---|---|
| Klebsiella pneumoniae L142 | >128 |
| Branhamella catarrhalis ATCC 8176 L76 | ≧64 |

| Strain | M.I.C. (microgram/ml) Antibiotic GE 2270 factor $A_2$ |
|---|---|
| Staph. aureus Tour L165 | 1 |
| Staph. aureus Tour L165 + 30% bovine serum | 2 |
| Staph. epidermidis L147 ATCC 12228 | 2 |
| Staph. haemolyticus L602 clin. isolate | 4 |
| Strep. pyogenes C203 | >128 |
| Strep. pneumoniae UC41 | >128 |
| Strep. faecalis ATCC 7080 | 0.5 |
| Strep. mitis L796 | 8 |
| Clostridium perfringens ISS 30543 | 0.06 |
| Propionibacterium acnes ATCC 6919 | 0.06 |
| Bacteroides fragilis ATCC 23745 | 128 |
| Neisseria gonorrhoeae ISM68/126 | >128 |
| Haemophilus influenzae type b ATCC19418 | >128 |
| Ureaplasma urealyticum L 1479 | >128 |
| Escherichia coli 12140 | >128 |
| Pseudomonas aeruginosa ATCC 10145 | >128 |
| Proteus vulgaris ATCC 881 | >128 |

| Strain | M.I.C. (microgram/ml) Antibiotic GE 2270 factor $A_3$ |
|---|---|
| Staph. aureus Tour L165 | 0.5 |
| Staph. aureus Tour L165 + 30% bovine serum | 2 |
| Staph. epidermidis L147 ATCC 12228 | 1 |
| Staph. haemolyticus L602 clin. isolate | 2 |
| Strep. pyogenes C203 | 8 |
| Strep. pneumoniae UC41 | 0.5 |
| Strep. faecalis ATCC 7080 | 1 |
| Clostridium perfringens ISS 30543 | ≦0.03 |
| Propionibacterium acnes ATCC 6919 | ≦0.03 |
| Bacteroides fragilis ATCC 23745 | 8 |
| Neisseria gonorrhoeae ISM68/126 | 8 |
| Haemophilius influenzae type b ATCC19418 | 4 |
| Ureaplasma urealyticum L 1479 | >128 |
| Escherichia coli SKF 12140 | >128 |
| Pseudomonas aeruginosa ATCC 10145 | >128 |
| Proteus vulgaris ATCC 881 | >128 |
| Branhamella catarrhalis ATCC 8176 L 76 | 0.5 |
| Chlamydia trachomatis (oculo-genital clin. isol.) | 128 |

| Strain | M.I.C. (microgram/ml) Antibiotic GE 2270 factor H |
|---|---|
| Staph. aureus Tour L165 | 0.06 |
| Staph. aureus Tour L165 + 30% bovine serum | 0.25 |
| Staph. epidermidis L147 ATCC 12228 | 0.25 |
| Staph. haemolyticus L602 clin. isolate | 0.5 |
| Strep. pyogenes C203 | 4 |
| Strep. pneumoniae UC41 | 1 |
| Strep. faecalis ATCC 7080 | 0.06 |
| Strep. mitis L796 | 0.5 |
| Clostridium perfringens ISS 30543 | 0.03 |
| Propionibacterium acnes ATCC 6919 | 0.25 |
| Bacteroides fragilis ATCC 23745 | >64 |
| Neisseria gonorrhoeae ISM68/126 | >128 |
| Haemophilus influenzae type b ATCC 19418 | >128 |
| Ureaplasma urealyticum L 1479 | 32 |
| Escherichia coli SKF 12140 | >128 |
| Pseudomonas aeruginosa ATCC 10145 | >128 |
| Proteus vulgaris ATCC 881 | >128 |
| Klebsiella pneumoniae L142 | >128 |

The antimicrobial activity of the compounds of the invention is confirmed also in experimental septicemia in mice.

Groups of five CD1 mice of both sexes (Charles River, average weight 18–22 g) were infected intraperitoneally with Staphylococcus aureus ATCC 19636. The bacterial challenge ($10^6$ cells/mouse) was given suspended in 0.5 ml of 5% bacteriological mucin (Difco). The test compounds were administered intraveneously once immediately after infection in a sterile aqueous solution containing 5% dimethylformamide and 10% Chremophor ® EL (polyethoxylated castor oil).

The $ED_{50}$ was calculated on the seventh day from the percentage of surviving animals at each dose by the Spearman and Kaerber method; its value resulted 15.4 mg/kg for antibiotic GE 2270 factor $A_3$ and 3.2 mg/kg for antibiotic GE 2270 factor $A_1$.

In a similar experiment, but using groups of eight mice and administering a single dose level of test compound (20 mg/kg), the ratio survivors/treated at the seventh day was ⅛ in the case of antibiotic GE 2270 factor $A_2$ and 6/8 in the case of antibiotic GE 2270 factor H. The test compounds were given i.v. as a milky suspension in 10% dimethylformamide in 5% aqueous glucose.

In view of their properties, the compounds of the invention can be used as active ingredients in the preparation of medicaments for human or animal treatment.

In particular, antibiotic GE 2270 factor $A_1$, $A_2$, $A_3$ and H are antimicrobial agents mainly active against gram positive bacteria and gram positive as well as gram negative anaerobes.

The main therapeutic indication of the antibiotic substances of the invention is thus in the treatment of infections related to the presence of microorganisms susceptible to them.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compounds of the invention can be administered as such or in admixture with pharmaceutically acceptable carriers and can also be administered in conjunction with other antimicrobial agents. Conjunctive therapy, thus includes sequential, simultaneous and separate administration of the active compounds in a way that the therapeutical effects of the first administered one is not entirely disappeared when the subsequent is administered.

A preferred pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such oleaginous ointment bases (e.g. cetyl esters wax, oleic acid, olive oil, paraffin, spermaceti, starch glycerite); absorbent ointment bases (e.g. anhydrous lanolin, hydrophilic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly(oxy-1,2-ethan ediyl)-alphahydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical Sciences, Seventeenth edition, 1985, Mack Publishing Co.

The compounds of the invention can also be formulated into formulation suitable for parenteral administration according to procedures known per se in the art. For instance, a compound of the invention is formulated with polypropylene glycol or dimethylacetamide and a surface-active agent such as polyoxyethylene sorbitan mono-oleate or polyethoxylated castor oil.

A preferred formulation for parenteral administration includes the following excipients: Cremophor® EL (polyoxyl 35 castor cil USP/NF) 20%, propylene glycol 5-10%.

Preferably, this formulation is used for i.v. administration in the treatment of any infection involving a microorganism susceptible to an antibiotic of the invention.

In the treatment of pseudomembranous colitis or other diseases attributable to the presence of anaerobes in the gastrointestinal tract, an effective dose of the compounds of the invention may be administered orally in suitable pharmaceutical form such as a capsule or an aqueous suspension.

The dosage of the active ingredient depends on many factors which include type, age and conditions of the patient, specific active ingredient and formulation selected for administration, administration schedule, etc.

In general, effective antimicrobial dosages are employed per single unit dosage form. Repeated applications of these dosage forms, e.g. from 2 to 6 times a day, are in general preferred. An effective dosage may be in general in the range 0.5-50 mg/kg body weight/day.

A preferred topic preparation is an ointment containing from 1% to 10% of a compound of the present invention.

Anyway, the prescribing physician will be able to determine the optimal dosage for a given patient in a given situation.

Besides their use as medicaments in human and veterinary therapy, the compounds of the invention can also be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., S. Francisco, USA, 1969 or "Livestock Feeds and Feeding" O and B books, Corvallis, Ore., USA, 1977).

The following examples further illustrate the invention and should not be interpreted as limiting it in any way.

EXAMPLE 1

PREPARATION OF ANTIBIOTIC GE 2270 FACTOR $A_1$ 1.1 1M Hydrochloric acid (3.3 ml) is added to a solution of 150 mg of antibiotic GE 2270 factor A in 16 ml of 95% ethanol. The mixture is kept at room temperature for 5 min, diluted with 0.1M sodium phosphate buffer pH 7.5 and then adjusted to pH 7.5 with sodium hydroxide. After concentration to aqueous phase under reduced pressure, this mixture is extracted twice with ethyl acetate. Then the organic phase (which contains mainly antibiotic GE 2270 factor $A_1$) is concentrated to a solid residue that is solubilized in 5 ml of tetrahydrofuran and then diluted with water to the solubility limit. This solution is purified in 10 subsequent HPLC runs using a column (250×20 mm) of Nucleosil® C 18 (5 micromole) reverse phase silica gel packed by Stacroma® eluting with a linear gradient from 64% to 93% of phase B in phase A, in 20 min, at a flow rate of about 15 ml/min. In this system, phase A is a 90:10 (v/v) mixture of 18 mM sodium phosphate pH 7.2 and acetonitrile, while phase B is a 40:60 (v/v) mixture of 18 mM sodium phosphate pH 7.2 and acetonitrile. Fractions are collected and UV monitored at 330 nm; those fractions which contain substantial amounts of antibiotic GE 2270 factor $A_1$, which correspond to the peaks of the UV plot, are pooled and concentrated under reduced pressure to aqueous phase which is extracted twice with ethyl acetate. This organic layer is then washed with distilled water to remove the residual inorganic salts and concentrated to a solid residue that is then dissolved in tetrahydrofuran and re-precipitated with petroleum ether, thus giving pure antibiotic GE 2270 factor $A_1$ (64 mg).

1.2 Antibiotic GE 2270 factor $A_1$ is the main reaction product of antibiotic GE 2270 factor A when this antibiotic is incubated for 15 min at room temperature in a 5/4/1 (v/v) mixture of diethylenedioxide, water and trifluoroacetic acid.

Antibiotic GE 2270 factor $A_1$ is also obtained when antibiotic GE 2270 factor A is incubated in 0.5 N sulfuric acid or 0.25M phosphoric acid in a 1/1 (v/v) mixture of diethylenedioxide and water at room temperature. After dilution with cold water and neutralization, the mixture is extracted with ethyl acetate, the organic phase is concentrated and a solid precipitated by adding petroleum ether.

Pure antibiotic GE 2270 factor $A_1$ is obtained by preparative HPLC as described in Example 1.1.

1.3 Antibiotic GE 2270 factor A1 is the main reaction product of antibiotic GE 2270 factor A when this antibiotic is incubated overnight at 50° C in 0.5M ammonium chloride in a 1:1 (v/v) mixture of diethylenedioxide/water. After dilution with cold water and neutralization, the mixture is extracted with ethyl acetate, the organic phase is concentrated and a solid precipitated by adding petroleum ether.

Pure antibiotic GE 2270 factor $A_1$ is obtained by preparative HPLC as described in Example 1.1.

EXAMPLE 2

PREPARATION OF ANTIBIOTIC GE 2270 FACTOR $A_2$ 2.1 Antibiotic GE 2270 factor A (86 mg) is dissolved in 17 ml of 95% ethanol and 1.7 ml of acetic acid. After incubation at 60° C. for 24 h, the resulting solution is diluted with 0.1M sodium phosphate buffer pH 7.5 (100 ml) and adjusted to pH 7.5 with 1M sodium hydroxide. Ethanol is removed by evaporation under reduced pressure and the aqueous residue is extracted twice with ethyl acetate (100 ml). The organic phase is concentrated under reduced pressure to obtain a solid residue which is solubilized with tetrahydrofuran and then precipitated by adding petroleum ether. Antibiotic GE 2270 factor $A_2$ (62 mg) is obtained with minor amounts of antibiotic GE 2270 factors A and $A_1$. Pure antibiotic GE 2270 factor $A_2$ is obtained by preparative HPLC as follows:

10 Mg of the above crude product is solubilized in tetrahydrofuran, diluted to the solubility limit with water and then injected into a HPLC system with a column (250×20 mm) packed with Nucleosil ® C18 (5 micrometer) reverse phase silica gel by Stacroma ®, eluting with a linear gradient from 64% to 93% of phase B in phase A, in 20 min, at a flow rate of about 15 ml/min. In this system, phase A is a 90:10 (v/v) mixture of 18 mM sodium phosphate pH 7.2 and acetonitrile, while phase B is a 40:60 (v/v) mixture of 18 mM sodium phosphate pH 7.2 and acetonitrile. Fractions of five consecutive runs are collected and UV monitored at 330 nm. Fractions which contain substantial amounts of antibiotic GE 2270 factor $A_2$, which correspond to the major peaks of the UV elution profile, are pooled and concentrated under reduced pressure to an aqueous phase which is extracted twice with ethyl acetate. This organic layer is then washed with distilled water to remove the residual inorganic salts and concentrated to precipitate a solid residue that is then dissolved in tetrahydrofuran and reprecipitated with petroleum ether, to obtain pure antibiotic GE 2270 factor $A_2$ (45 mg).

2.2 Antibiotic GE 2270 factor $A_2$ is the main reaction product of antibiotic GE 2270 factor A when this antibiotic is incubated overnight at 80° C. in a 1/1 (v/v) mixture of acetic acid and water. After dilution with water and neutralization, antibiotic GE 2270 factor $A_2$ is extracted with ethyl acetate, concentrated under reduced pressure and precipitated by adding petroleum ether.

Pure antibiotic GE 2270 factor $A_2$ derivative is obtained by preparative HPLC as described in Example 2.1.

2.3 Antibiotic GE 2270 factor $A_2$ is the main reaction product of antibiotic GE 2270 factor A when this antibiotic is incubated overnight at 50° C. in a 5/4/1 mixture (v/v) of diethylenedioxide, water and trifluoroacetic acid. Alternatively, the reaction may be conducted in the presence of inorganic acids such as 0.5N sulfuric acid or 0.25M phosphoric acid in a 1/1 (v/v) mixture of diethylenedioxide and water. After dilution with water and neutralization, antibiotic GE 2270 factor $A_2$ is extracted with ethyl acetate, concentrated under reduced pressure and precipitated by adding petroleum ether.

Pure antibiotic GE 2270 factor $A_2$ can be obtained by preparative HPLC as described in Example 2.1.

2.4 Antibiotic GE 2270 factor $A_z$ is the main reaction product of antibiotic GE 2270 factor A when this antibiotic, solubilized in a 1/1 (v/v) mixture of diethylenedioxide and water, is incubated overnight at 50° C. in the presence of an acidic cation exchange resin such as Dowex ® 50W×2 in the acid ionic form. Then the resin is removed from the reaction mixture and the solution is diluted with cold water and neutralized. Antibiotic GE 2270 factor $A_2$ is extracted with ethyl acetate, concentrated under reduced pressure and precipitated by adding petroleum ether.

Pure antibiotic GE 2270 factor $A_2$ can be obtained by preparative HPLC as described in Example 2.1.

2.5 Antibiotic GE 2270 factor $A_2$ is also obtained from antibiotic GE 2270 factor $A_1$ when this antibiotic is treated in the conditions described for GE 2270 factor A in Examples 2.1, 2.2, 2.3 or 2.4.

Generally, a molar yield of 60–85% is obtained in this reaction.

EXAMPLE 3

PREPARATION OF ANTIBIOTIC GE 2270 FACTOR $A_3$ 3.1 Antibiotic GE 2270 factor $A_2$ is incubated for 1 h at room temperature in 0.5M sodium carbonate. The reaction mixture is then diluted with cold water and brought to pH 6.5 with hydrochloric acid. The neutralized solution contains antibiotic GE 2270 factor $A_3$ as the main reaction product. This antibiotic is extracted from the aqueous phase with ethyl acetate and then is precipitated from the concentrated organic phase by adding petroleum ether.

Pure antibiotic GE 2270 factor $A_3$ is obtained by column chromatography as described below.

3.2 1.5 Grams of crude GE 2270 $A_3$ is dissolved in 60 ml of a 1/1 (v/v) mixture of methanol and dichloromethane and adsorbed on silica gel (75–230 mesh) by evaporation of the solvents under reduced pressure. The solid residue is then put on the top of a silica gel (75–230 mesh) column (bed height 40 cm) equilibrated with dichloromethane. The column is then eluted with mixtures of methanol in dichloromethane in the order: 1) 2% methanol (450 ml); 2) 5% methanol (500 ml); 3) 10% methanol (600 ml); 4) 15% methanol (500 ml); 5) 20% methanol (500 ml); 6) 30% methanol (250 ml).

Fractions are collected and monitored by TLC and a microbiological assay on *B. subtilis* ATCC 6633. Antibiotic GE 2270 factor $A_3$ is normally present in the eluates which contain about 15–20% methanol.

The fractions containing the desired product are pooled and concentrated under reduced pressure. Upon addition of petroleum ether to the residue, antibiotic GE 2270 factor $A_3$ precipitates (854 mg of pure product).

3.3 Antibiotic GE 2270 factor A solubilized in a 1/1 (v/v) mixture of diethylenedioxide and water is incubated for 40 h in the presence of a cation exchange resin (Dowex ® 50W×2) in the $H^+$ form. The resin is then removed and the reaction solution is diluted with cold water and brought to pH 6.5 with aqueous sodium hydroxide. This mixture is extracted with ethyl acetate and precipitated from the concentrated organic phase by adding petroleum ether. Antibiotic GE 2270 factor $A_3$ is then isolated and purified by column chromatography as described in Example 3.2. (Global molar yield: 15%).

EXAMPLE 4

PREPARATION OF ANTIBIOTIC GE 2270 FACTOR H 4.1 500 Mg of sodium borohydride and 250 mg of antibiotic GE 2270 factor A are dissolved in 100 ml of a 1/1 (v/v) mixture of tetrahydrofuran and water. After three days at room temperature, the solution is brought to about pH 7 with a 1M $NaH_2PO_4$ and then concentrated under reduced pressure. The water is extracted twice with ethyl acetate and the organic phase is concentrated to dryness. The solid residue, that contains mainly antibiotic GE 2270 factor H, is dissolved in tetrahydrofuran and then precipitated by adding petroleum ether thus yielding 213 mg of a white precipitate which is purified by preparative HPLC as follows:

10 Mg of crude reaction product is solubilized in tetrahydrofuran, diluted to the solubility limit with water and then injected into a HPLC column (250×20 mm) of Nucleosil® C18 (5 micrometer) reverse phase silica gel packed by Stacroma eluting with a linear gradient from 64% to 93% of phase B in phase A, in 20 min, at a flow rate of about 15 ml/min. Then elution is continued for 5 min with phase B alone. In this system, phase A is a 90:10 (v/v) mixture of 18 mM sodium phosphate pH 7.2 and acetonitrile, while phase B is a 40:60 (v/v) mixture of 18 mM sodium phosphate pH 7.2 and acetonitrile. Fractions of ten consecutive runs are collected and UV monitored at 330 nm; those fractions which contain substantial amounts of antibiotic GE 2270 factor H, which correspond to the peaks of the UV elution profile, are pooled and concentrated under reduced pressure to an aqueous phase which is extracted twice with ethyl acetate. This organic layer is then washed with distilled water to remove the residual inorganic salts and concentrated to precipitate a solid residue. This is then dissolved in tetrahydrofuran and re-precipitated with petroleum ether, to obtain pure antibiotic GE 2270 factor H (55 mg).

PREPARATION OF STARTING MATERIALS

The starting materials are prepared by following the procedures outlined in European Patent Application Publication No. 359062.

BRIEF DESCRIPTION OF THE DRAWINGS

The symbols used in the attached U.V. spectra have the following meanings:
refers to the assay in 0.1 N HCl
refers to the assay in 0.1 N KOH
refers to the assay in methanol
refers to assay in phosphate buffer pH 7.4

Figure 1:
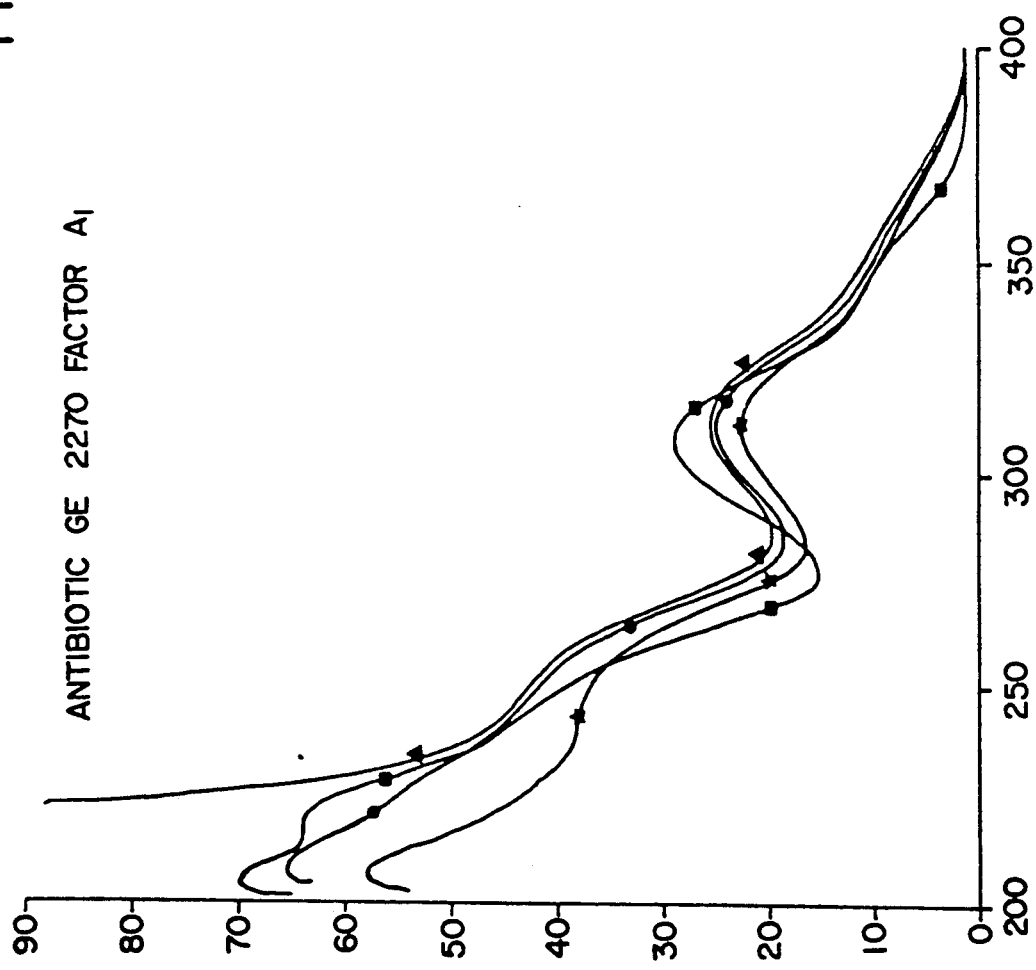
Figure 2:
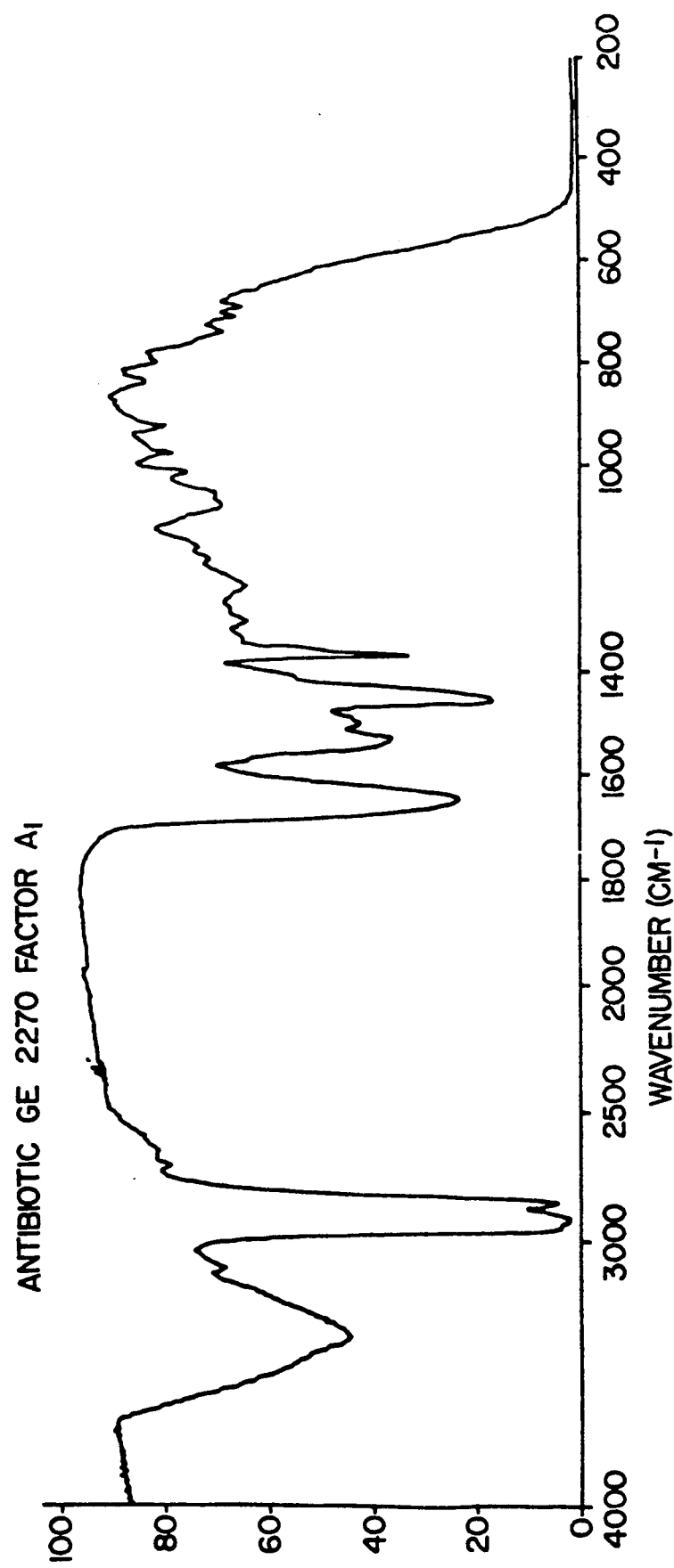
Figure 3:
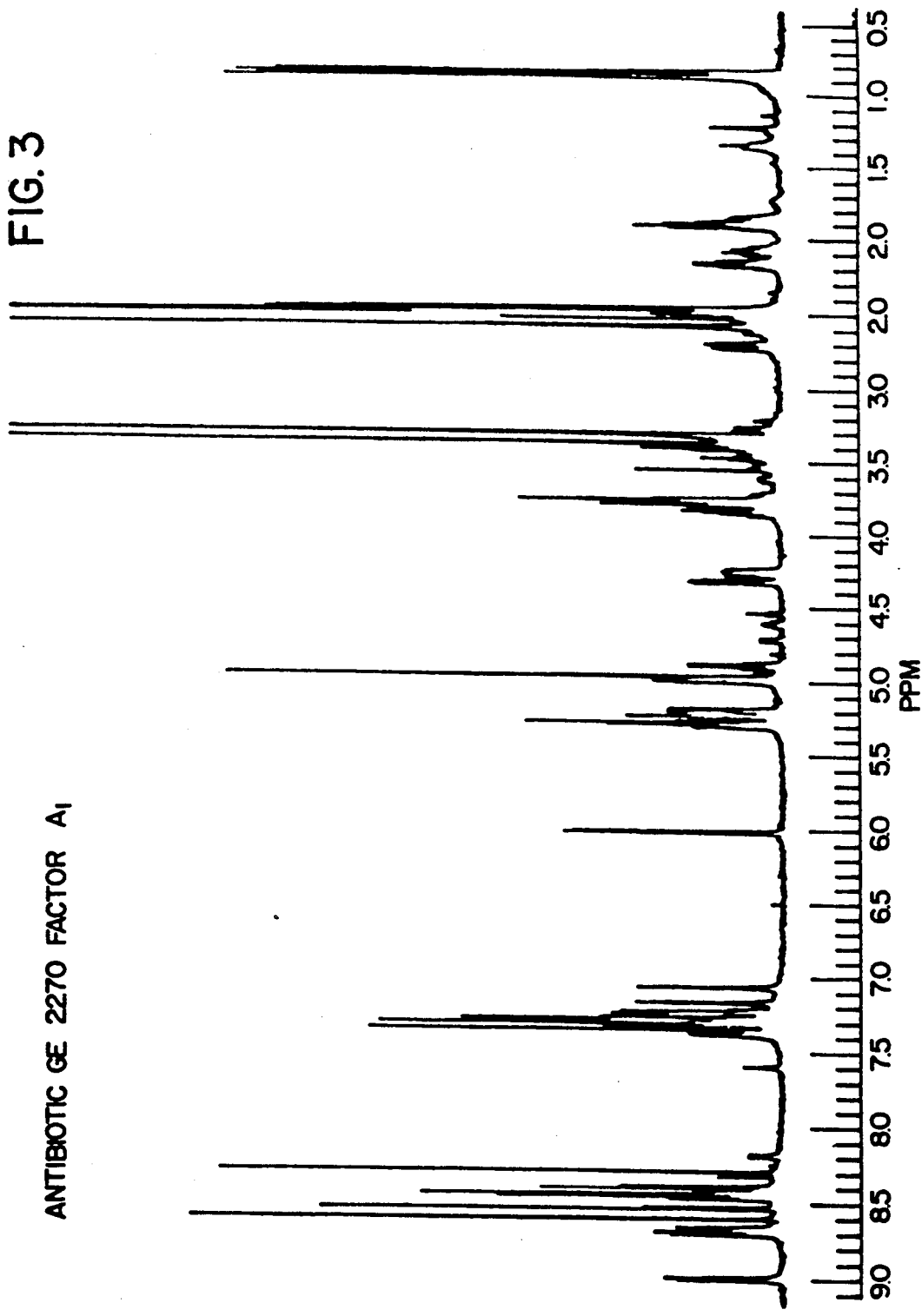
Figure 4:
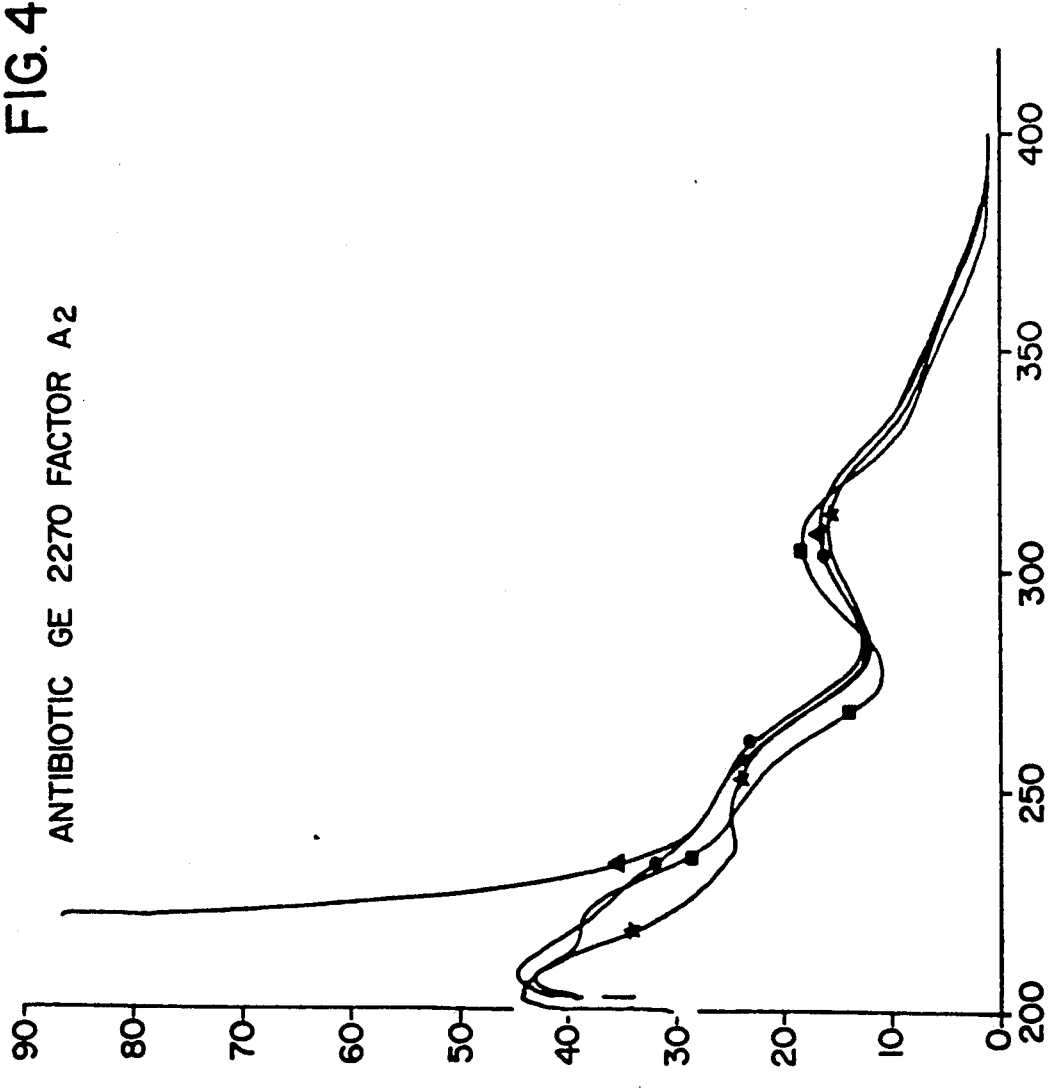
Figure 5:
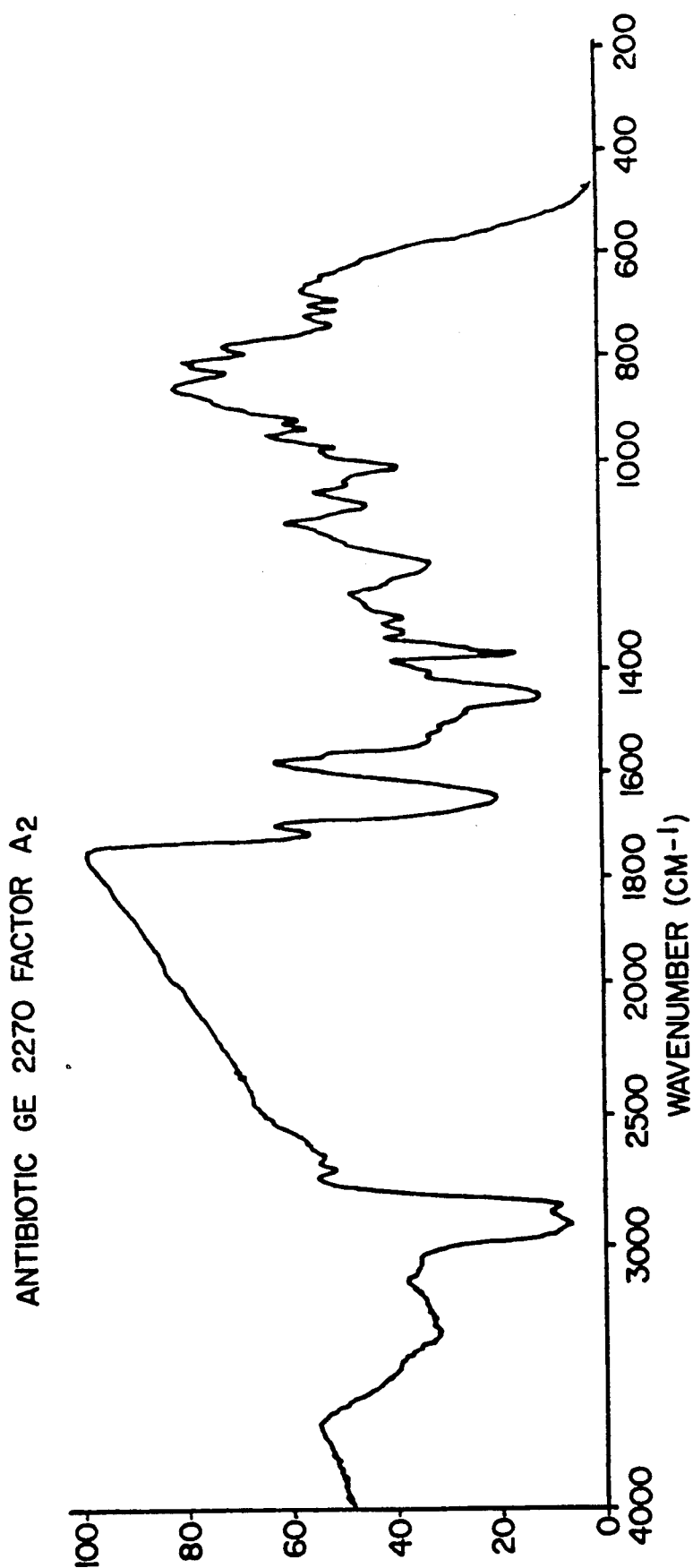
Figure 6:
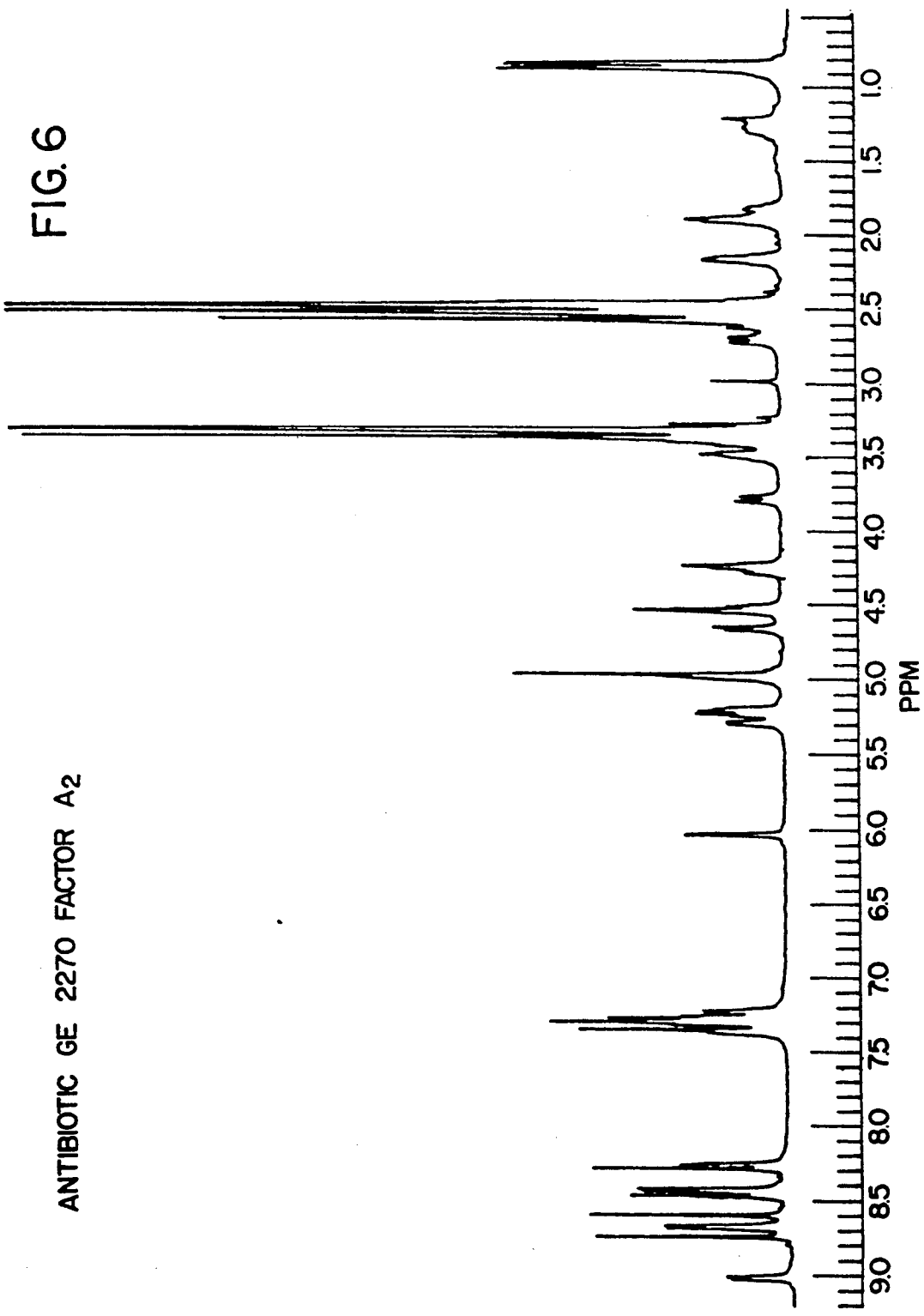
Figure 7:
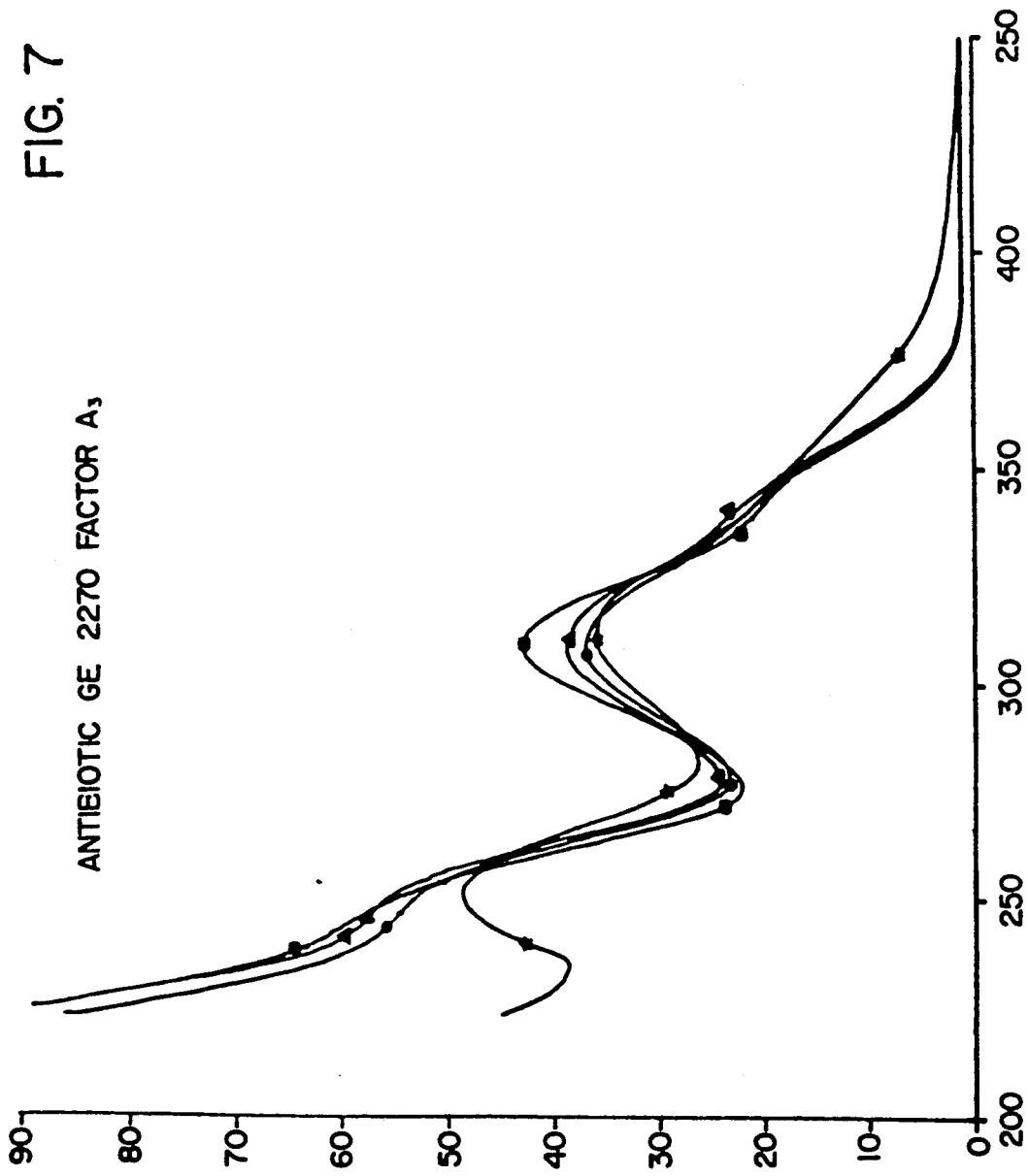
Figure 8:
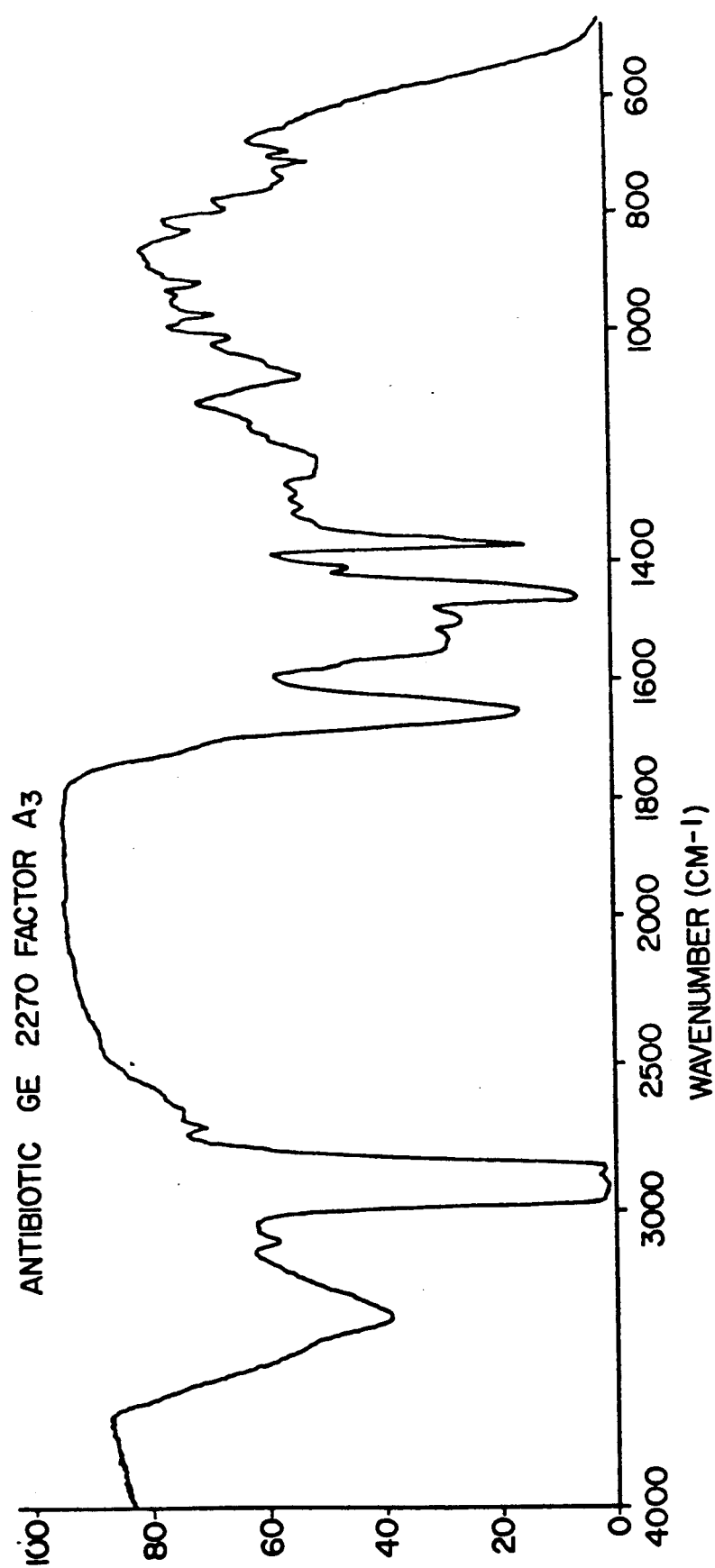
Figure 9:
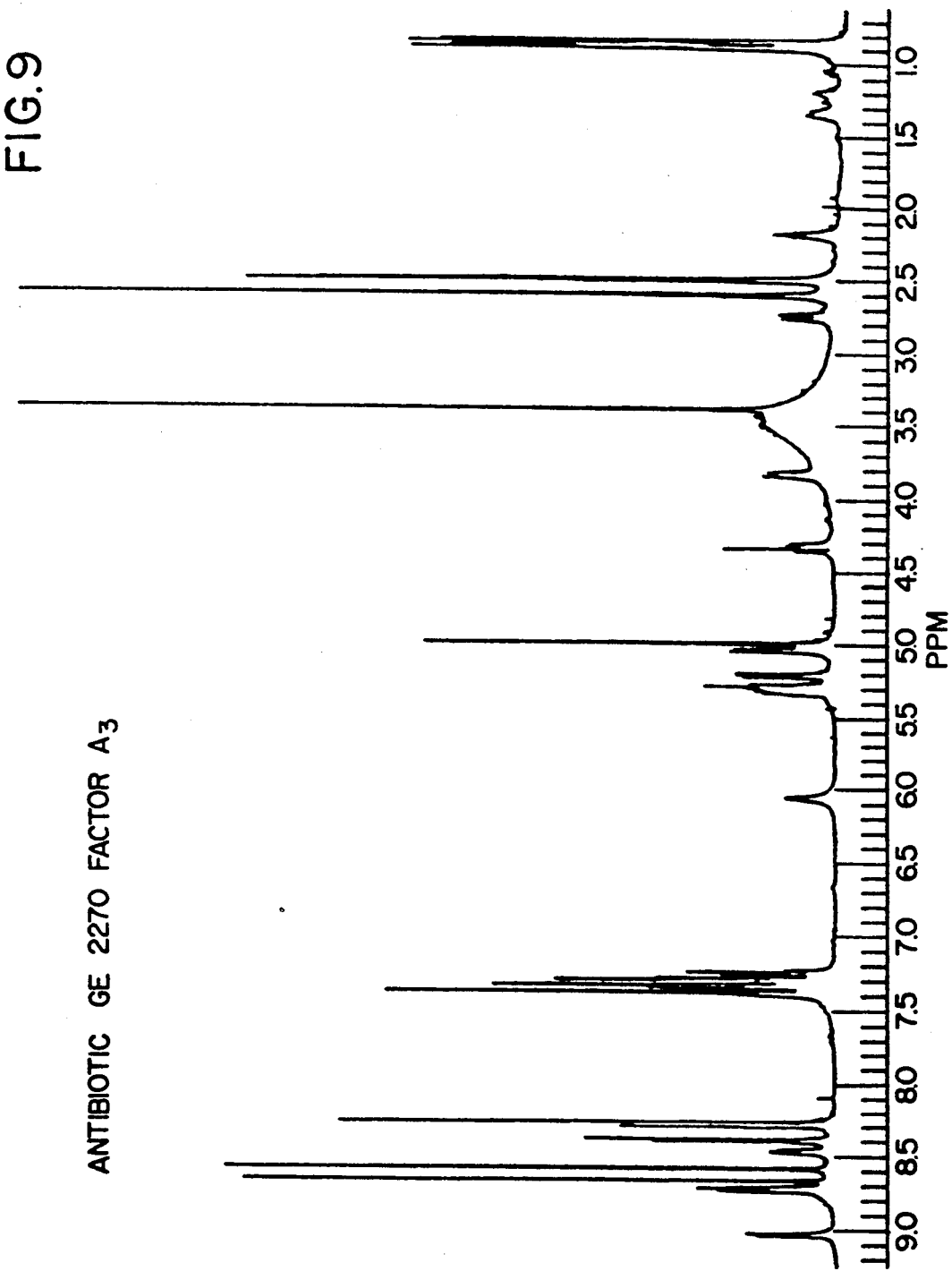
Figure 10:
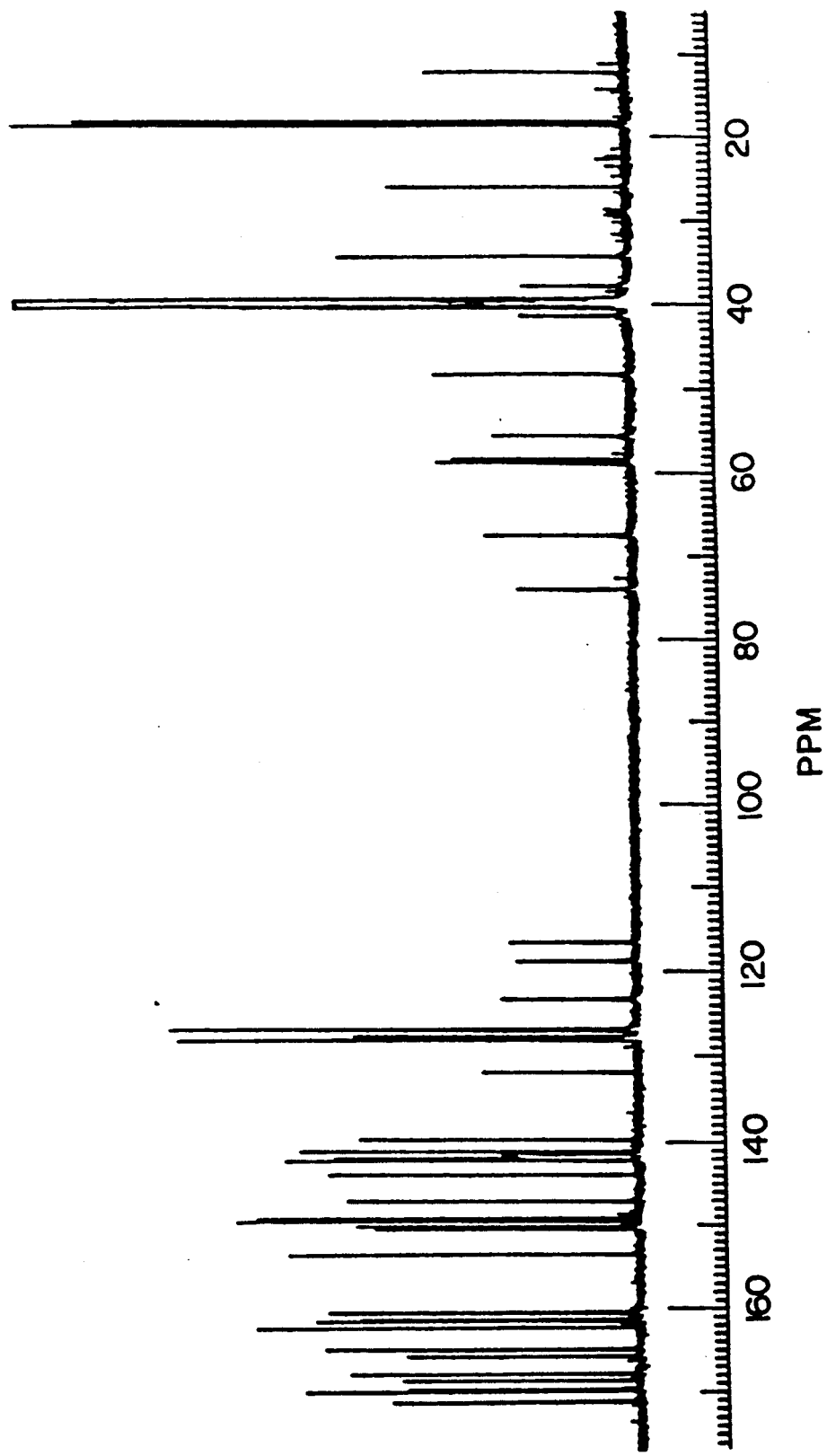
Figure 11:
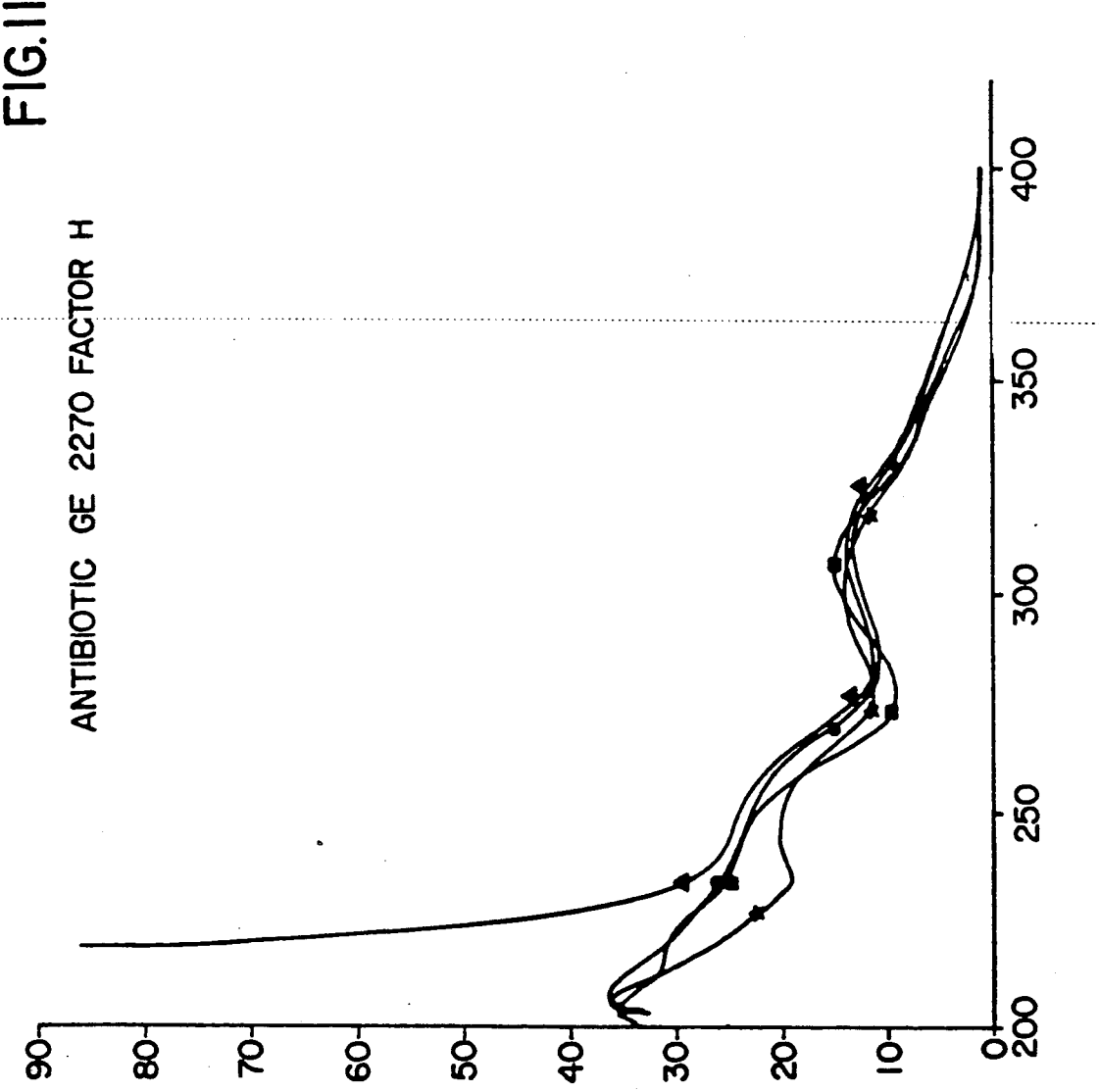
Figure 12:
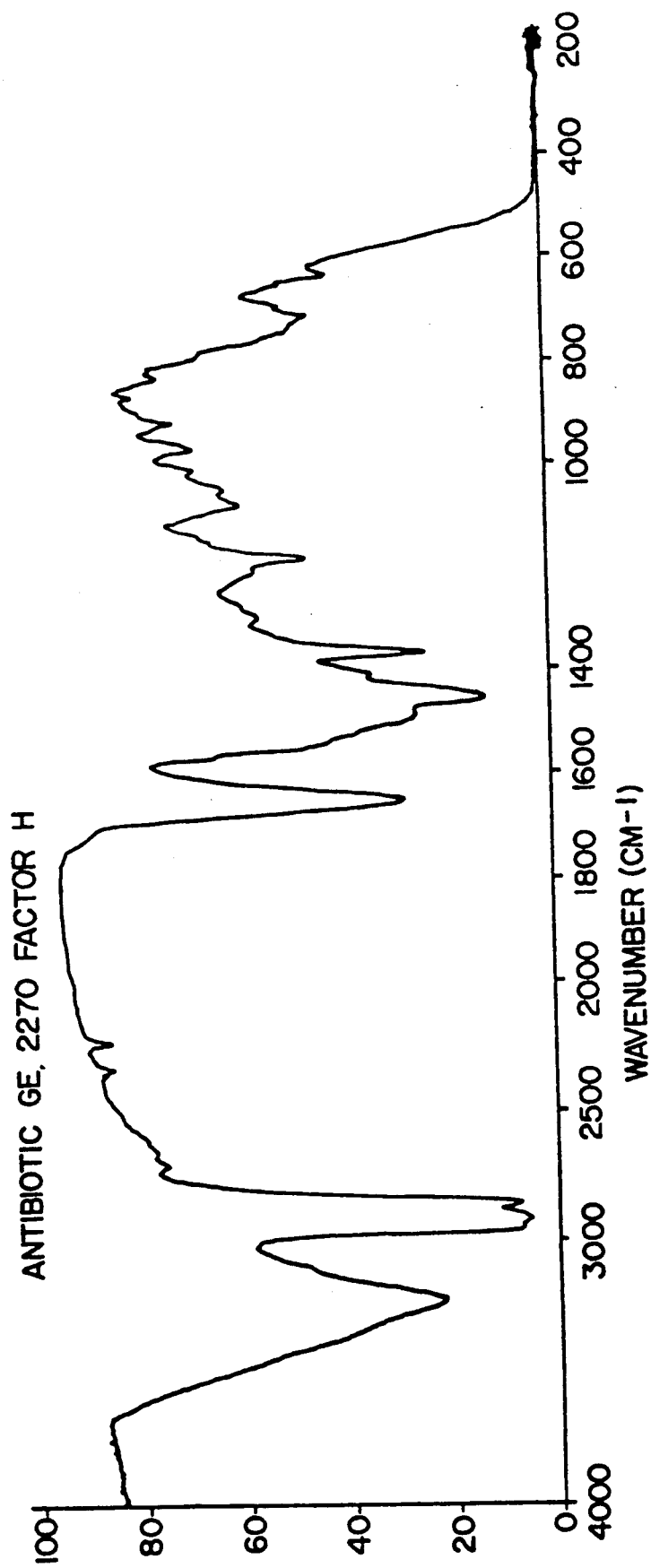
Figure 13:
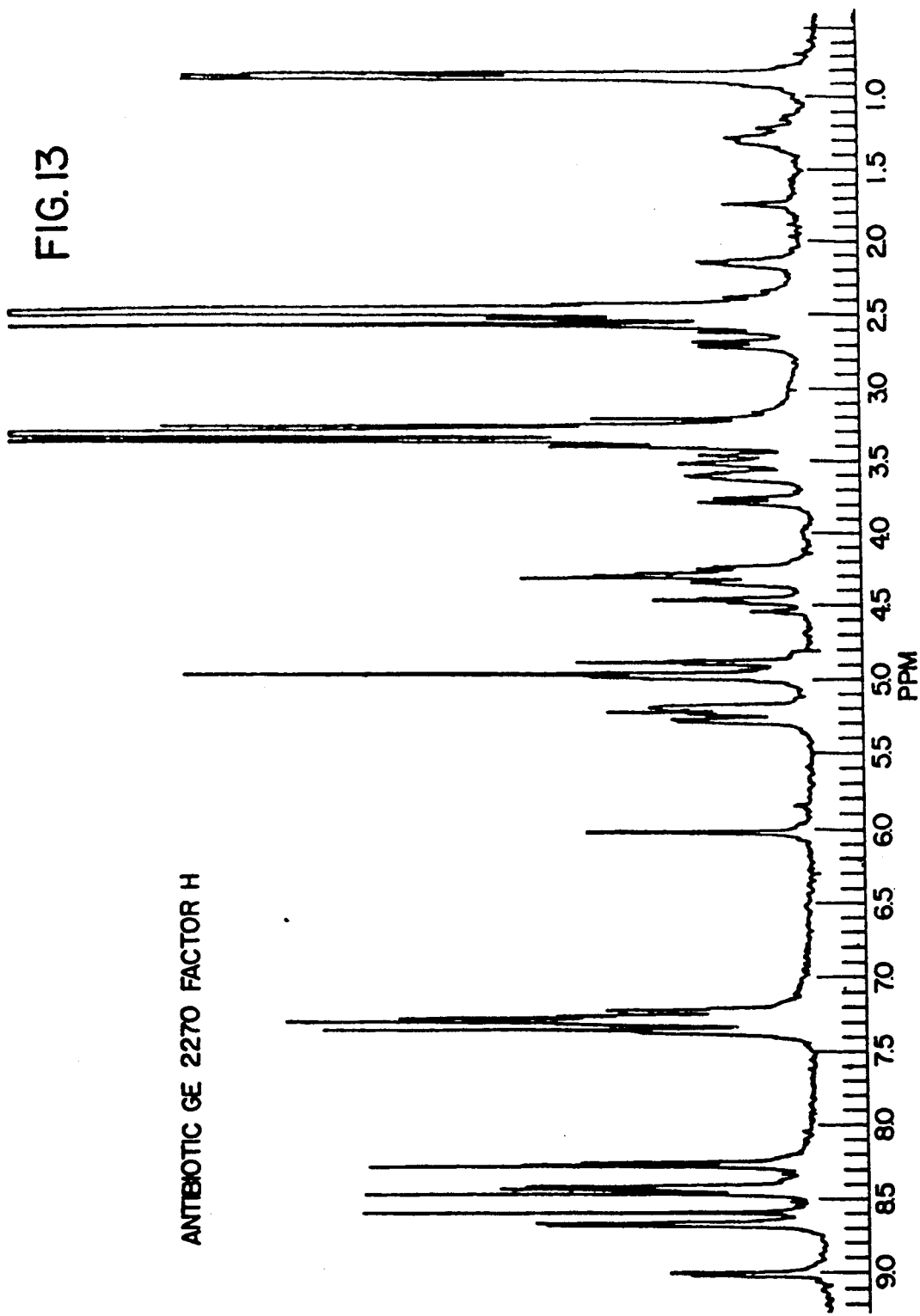

We claim:

1. An antibiotic substance selected from antibiotic GE 2270 factors $A_1$, $A_2$, $A_3$ or H, and the acceptable salts thereof, which have the following features in the unsalified form:

Physico-chemical characteristics of antibiotic GE 2270 factor $A_1$:

A) ultraviolet absorption spectrum which exhibits the following absorption maxima:

| | Lambda max (nm) |
|---|---|
| 0.1M HCl | about 240 (shoulder) |
| | 310 |
| 0.1M KOH | about 245 (shoulder) |
| | 311 |
| Phosphate buffer pH 7.4 | about 245 (shoulder) |
| | 310 |
| Methanol | about 215 (shoulder) |
| | about 240 (shoulder) |
| | 309 |

B) infrared absorption spectrum in nujol mull which exhibits the following absorption maxima (cm$^{-1}$):
3700–3000; 3000–2800 (nujol); 1650; 1535; 1505; 1460 (nujol); 1375 (nujol); 1310; 1240; 1190; 1165; 1130–1000; 980; 930; 840; 805; 750; 720 (nujol); 700;

C) $^1$H-NMR spectrum which exhibits the following groups of signals at 500 MHz recorded in DMSO D$_6$ (hexadeuterodimethylsulfoxide) using TMS as the internal standard (0.00 ppm); the multiplicity for each signal is also reported below (s=singlet; d=doublet; m=multiplet; dd=doublet of doublets; br s=broad singlet):
0.84, d; 0.87, d; 1.35, m; 1.91, m; 2.08, m; 2.16, m; 2.46, d; 2.58, s; 2.70, dd; 3.38, s; 3.76, m; 3.84, m; 4.26, dd; 4.33, m; 4.89, m; 4.97, s; 5.00, dd; 5.20, dd; 5.22, dd; 5.28 (2 protons), m; 6.01, d; 7.07, s; 7.2, s; 7.34, s; 7.22-7.38 (6 protons), m; 8.29, s; 8.39, d; 8.44, m; 8.45, d; 8.54, s; 8.60, s; 8.66, d; 9.69, d; 8.99, d.

D) retention-time (R$_t$) of 13.4 min when analyzed by reverse phase HPLC under the following conditions:
column: Ultrasphere ODS (reverse phase silanized silica gel; 5 micrometer) Altex (Beckman) 4.6 mm (i.d.)×250 mm
pre-column: Brownlee Labs RP 18 (octadecylsilane silica gel; 5 micrometer)
eluent A: acetonitrile:18mM NaH$_2$PO$_4$, 70:30 (v/v), adjusted to pH 7.0
eluent B: acetonitrile:18mM NaH$_2$PO$_4$ 10:90 (v/v), adjusted to pH 7.0
elution mode: linear gradient of eluent A in eluent B from 45% to 70% in 20 min
flow rate: 1.8 ml/min
U.V. detector: 254 nm
internal standard: Chloramphenicol (R$_t$=3.6 min)

E) elemental analysis, after the sample has been previously dried at about 140° C. under inert atmosphere, which indicated the following composition: carbon, hydrogen, nitrogen, sulfur.

F) FAB-MS analysis showing the low mass isotope of the protonated molecular ion at m/z 1308 mass units; all the other peaks above 800 m/z mass units in the spectrum, not counting isotope peaks, were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode Physico-chemical characteristics of antibiotic GE 2270 factor $A_2$:

A) ultraviolet absorption spectrum which exhibits the following absorption maxima:

| | Lambda max (nm) |
|---|---|
| 0.1M HCl | about 245 (shoulder) |
| | 309 |
| 0.1M KOH | about 245 (shoulder) |
| | 309 |
| Phosphate buffer pH 7.4 | about 245 (shoulder) |
| | 309 |
| Methanol | about 215 (shoulder) |
| | about 242 (shoulder) |
| | 306 |

B) infrared absorption spectrum in nujol mull which exhibits the following absorption maxima (cm$^{-1}$):
3700–3000; 3000–2800 (nujol); 1725; 1655; 1590–1480; 1460 (nujol); 1410; 1375 (nujol); 1335; 1305; 1265–1130; 1090; 1050; 1015; 980; 945; 930; 840; 805; 745; 720 (nujol); 700;

C) $^1$H-NMR spectrum which exhibits the following groups of signals at 500 MHz recorded in DMSO-D$_6$ hexadeuterodimethylsulfoxide) using TMS as the internal standard (0.00 ppm); the multiplicity for each signal is reported between parenthesis (s=singlet; d=doublet; m=multiplet; dd=doublet of doublets; br s=broad singlet):
0.83, d; 0.86, d; 1.30, m; 1.82, m;; 1.90, m; 2.17, m; 2.46, d; 2.57, s; 2.70, dd; 3.37, s; 3.40, m; 3.48, m; 3.77, dd; 4.24, m; 4.28, dd; 4.52, d; 4.53, br s; 4.67, d; 4.96, s;

4.98, dd; 5.19, m; 5.21, m; 5.28, m; 6.01, d; 7.34, s; 7.22–7.35, m; 8.26, d; 8.28, s; 8.42, d; 8.45, s; 8.59, s; 8.67 (2 protons), d; 8.73, s; 9.00, d;

D) retention-time ($R_t$) of 17.0 min when analyzed by reverse phase HPLC under the following conditions:

column: Ultrasphere ODS (reverse phase silanized silica gel; 5 micrometer) Altex (Beckman) 4.6 mm (i.d.)×250 mm
  pre-column: Brownlee Labs RP 18 (octadecylsilane silica gel; 5 micrometer)
  eluent A: acetonitrile:18mM $NaH_2PO_4$, 70:30 (v/v), adjusted to pH 7.0
  eluent B: acetonitrile:18mM $NaH_2PO_4$ 10:90 (v/v), adjusted to pH 7.0
  elution mode: linear gradient of eluent A in eluent B from 45% to 70% in 20 min
  flow rate: 1.8 ml/min
  U.V. detector: 254 nm
  internal standard: Chloramphenicol ($R_t$=3.6 min)

E) elemental analysis, after the sample has been previously dried at about 140° C. under inert atmosphere, which indicated the following composition: carbon, hydrogen, nitrogen, sulfur.

F) FAB-MS analysis showing the low mass isotope of the protonated molecular ion at m/z 1291 mass units; all the other peaks above 800 M/Z mass units in the spectrum, not counting isotope peaks, were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode Physico-chemical characteristics of antibiotic GE 2270 factor $A_3$:

A) ultraviolet absorption spectrum which exhibits the following absorption maxima:

|  | Lambda max (nm) |
|---|---|
| 0.1M KOH | 240 (shoulder) |
|  | 309 |
|  | 330 (shoulder) |
| Phosphate buffer pH 7.4 | 240 (shoulder) |
|  | 309 |
|  | 330 shoulder |
| Methanol | 240 (shoulder) |
|  | 309 |
|  | 340 (shoulder) |

B) infrared absorption spectrum in nujol mull which exhibits the following absorption maxima ($cm^{-1}$): 3700–3140; 3110; 3020–2750 (nujol); 1720; 1655; 1590–1520; 1500; 1460 (nujol); 1375 (nujol) 1270–1200; 1130–1030; 1020; 980; 930; 840; 805; 750; 720 (nujol); 700;

$^1$H-NMR spectrum which exhibits the following groups of signals (in ppm) at 500 MHz recorded in DMSO-$D_6$ hexadeuterodimethylsulfoxide) using TMS as the internal standard (0.00 ppm); the number of protons and multiplicity for each signal is also reported below (s=singlet; d=doublet; m=multiplet; dd=doublet of doublets; br s=broad singlet): 9.02,1H (d); 8.71,1H (d); 8.70,1H (d); 8.65,1H (s); 8.57,1H (s); 8.46,1H (m); 8.38,1H (d); 8.28,1H (d); 8.25,1H (s); 7.38,1H (m); 7.37,1H (s); 7.36–7.20,5H (m); 6.05,1H (br s); 5.31,1H (m); 5.27,1H (dd); 5.20,1H (dd); 5.03,1H (d); 4.99,2H (s); 4.32,1H (dd); 3.82,1H (dd); 3.38,3H (s); 2.74,1H (dd); 2.60,3H (s); 2.49,3H (d); 2.17,1H (m); 1.35,1H (m); 0.88,3H (d); 0.84,3H (d);

D) retention-time ($R_t$) of 7.1 min when analyzed by reverse phase HPLC under the following conditions:

column: Ultrasphere ODS (reverse phase silanized silica gel; 5 micrometer) Altex (Beckman) 4.6 mm (i.d.)×250 mm
  pre-column: Brownlee Labs RP 18 (octadecylsilane silica gel; 5 micrometer)
  eluent A: acetonitrile:18mM $NaH_2PO_4$, 70:30 (v/v), adjusted to pH 7.0
  eluent B: acetonitrile:18mM $NaH_2PO_4$ 10:90 (v/v), adjusted to pH 7.0
  elution mode: linear gradient of eluent A in eluent B from 45% to 70% in 20 min
  flow rate: 1.8 ml/min
  U.V. detector: 254 nm
  internal standard: Chloramphenicol (Rt =3.6 min)

E) elemental analysis, after the sample has been previously dried at about 140° C. under inert atmosphere, which indicated the following composition: carbon 51.27%, hydrogen 4.02%, nitrogen 14.94%, sulfur.

F) FAB-MS analysis showing the low mass isotope of the protonated molecular ion at m/z 1125 mass units; all the other peaks above 800 m/z mass units in the spectrum, not counting isotope peaks, were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode G) $^{13}$C-NMR spectrum exhibiting the following groups of signals (ppm) at 125 MHz in DMSO-$d_6$ TMS as the internal reference (0.00 ppm), 171.2; 169.9; 169.6; 168.5; 167.8; 165.7; 164.8; 162.2; 161.4; 161.3; 160.5; 160.4; 153.5; 150.4; 160.1; 149.5; 149.1; 147.0; 143.8; 142.1; 141.8; 141.4; 141.0; 139.6; 131.8; 128.0 (2 carbons); 127.7; 127.6; 126.9; 126.8 (2 carbons); 123.1; 118.7; 116.4; 73.9; 67.4; 58.7; 58.3; 55.5; 48.2; 41.2; 37.7; 34.1; 25.9; 18.5; 18.0; 12.0;

H) a specific optical rotation $[\alpha]^{20}_D$ of +182.5 in $CHCl_3$ +10% $CH_3OH$ Physico-chemical characteristics of antibiotic GE 2270 factor H:

A) ultraviolet absorption spectrum which exhibits the following absorption maxima:

|  | Lambda max (nm) |
|---|---|
| 0.1M HCL | 248 |
|  | 303 |
| 0.1M KOH | about 245 (shoulder) |
|  | 310 |
| Phosphate buffer pH 7.4 | about 240 (shoulder) |
|  | 312 |
| Methanol | about 215 (shoulder) |
|  | about 240 (shoulder) |
|  | 309 |

B) infrared absorption spectrum in nujol mull which exhibits the following absorption maxima ($cm^{-1}$): 3700–3000; 3000–2800 (nujol); 1655; 1590–1480; 1460 (nujol) 1375 (nujol); 1310; 1220; 1190; 1130–1000; 980; 930; 840; 820–680; 720 (nujol); 640;

C) $^1$H-NMR spectrum which exhibits the following groups of signals (ppm) at 500 MHz recorded in DMSO-D$_6$ (hexadeuterodimethylsulfoxide) using TMS as the internal standard (0.00 ppm); the multiplicity for each signal is also reported below (s=singlet; d=doublet; m=multiplet; dd=doublet of doublets; br s=broad singlet):

0.83, d; 0.87 d; 1.30, m; 2.16, m; 2.46, d; 2.58, s; 2.70, dd; 3.38, s; 3.52, m; 3.61, m; 3.77, dd; 4.25, m; 4.30, m; 4.35, m; 4.47, m; 4.88, m; 4.97, s; 4.99, dd; 5.20, m; 5.23, m; 5.28, m; 6.02, d; 7.36, s; 7.22–7.40, m; 8.26, d; 8.28, s; 8.42, d; 8.43, m; 8.47, s; 8.60, s; 8.67, d; 9.02, d;

D) retention-time ($R_t$) of 18.0 min when analyzed by reverse phase HPLC under the following conditions:
   column: Ultrasphere ODS (reverse phase silanized silica gel; 5 micrometer) Altex (Beckman) 4.6 mm (i.d.)×250 mm
   pre-column: Brownlee Labs RP 18 (octadecylsilane silica gel; 5 micrometer)
   eluent A: acetonitrile:18mM NaH$_2$PO$_4$, 70:30 (v/v), adjusted to pH 7.0
   eluent B: acetonitrile:18mM NaH$_2$PO$_4$ 10:90 (v/v), adjusted to pH 7.0
   elution mode: linear gradient of eluent A in eluent B from 45% to 70% in 20 min
   flow rate: 1.8 ml/min
   U.V. detector: 254 nm
   internal standard: Chloramphenicol ($R_t$=3.6 min)

E) elemental analysis, after the sample has been previously dried at about 140° C. under inert atmosphere, which indicated the following composition: carbon, hydrogen, nitrogen, sulfur.

F) FAB-MS analysis showing the low mass isotope of the protonated molecular ion at m/z 1180 mass units; all the other peaks above 800 m/z mass units (not counting isotope peaks) in the spectrum were lower than 20% of the molecular ion, upon analysis with a Kratos MS-50 double focusing mass spectrometer under the following experimental conditions: Xe fast atom bombardment at 6 Kv; 0.6 mA discharge current; glycerol matrix; positive ionization mode.

2. An antibiotic substance according to claim 1 wherein said antibiotic substance is antibiotic GE 2270 factor A$_1$.

3. An antibiotic substance according to claim 1 wherein said antibiotic substance is antibiotic GE 2270 factor A$_2$.

4. An antibiotic substance according to claim 1 wherein said antibiotic substance is antibiotic GE 2270 factor A$_3$.

5. An antibiotic substance according to claim 1 wherein said antibiotic substance is antibiotic GE 2270 factor H.

6. An pharmaceutical composition comprising an antibacterially effective amount of a compound of claim 1 in admixture with a pharmaceutically acceptable carrier.

7. A method for the treatment of bacterial infections comprising administering an antimicrobially effective amount of an antibiotic substance according to claim 1 to a patient in need thereof.

8. A method according to claim 7 wherein said antibiotic substance is antibiotic GE 2270 factor A$_1$.

9. A method according to claim 7 wherein said antibiotic substance is antibiotic GE 2270 factor A$_2$.

10. A method according to claim 7 wherein said antibiotic substance is antibiotic GE 2270 factor A$_3$.

11. A method according to claim 7 wherein said antibiotic substance is antibiotic GE 2270 factor H.

* * * * *

UNITED STATES PATENT AND TRADEMARK OFFICE
CERTIFICATE OF CORRECTION

PATENT NO. : 5,139,778

DATED : August 18, 1993

INVENTOR(S) : Selva, et al.

It is certified that error appears in the above-identified patent and that said Letters Patent is hereby corrected as shown below:

Column 15, line 51 of the patent "Az" should read --$A_2$--.

Column 17, lines 30-33 of the patent, only the definitions of the symbols were printed, not the actual symbols; lines 30-33 of the patent should read as follows:

--

 refers to the assay in 0.1 N HCl

 refers to the assay in 0.1 N KOH

 refers to the assay in methanol

 refers to assay in phosphate buffer pH 7.4--

UNITED STATES PATENT AND TRADEMARK OFFICE
CERTIFICATE OF CORRECTION

PATENT NO. : 5,139,778
DATED : August 18, 1993
INVENTOR(S) : Selva, et al

Page 2 of 2

It is certified that error appears in the above-indentified patent and that said Letters Patent is hereby corrected as shown below:

Column 20, line 40, "150.4; 160.1; 149.5;" should read --150.4; 150.1; 149.5;--.

Signed and Sealed this

Thirtieth Day of May, 1995

Attest:

BRUCE LEHMAN

*Attesting Officer*     *Commissioner of Patents and Trademarks*